(12) United States Patent
Frazao Moniz Pereira et al.

(10) Patent No.: US 6,833,135 B1
(45) Date of Patent: Dec. 21, 2004

(54) **DNA INTEGRATION INTO "*MYCOBACTERIUM* SPP." GENOME BY TRANS-COMPLEMENTATION USING A SITE-SPECIFIC INTEGRATION SYSTEM**

(75) Inventors: Jose A. Frazao Moniz Pereira, Lisboa (PT); Alcino Freitas Vieira, Lisboa (PT); Elsa M. Ribeiro Dos Santos-Anes, Portela-Loures (PT); Miguel A. Da Costa Garcia, Amadora (PT); Paulo J. Da Silva Alves, Santo Andre (PT)

(73) Assignee: Laboratorio Medinfar Produtos Farmaceuticos, LDA., Amadoro (PT)

( * ) Notice: Subject to any disclaimer, the term of this patent is extended or adjusted under 35 U.S.C. 154(b) by 0 days.

(21) Appl. No.: 09/269,717

(22) PCT Filed: Aug. 6, 1997

(86) PCT No.: PCT/PT97/00005

§ 371 (c)(1),
(2), (4) Date: Jun. 3, 1999

(87) PCT Pub. No.: WO99/07861

PCT Pub. Date: Feb. 18, 1999

(51) Int. Cl.$^7$ .................. A61K 39/04; A61K 39/02; A01N 63/00; C12N 1/12
(52) U.S. Cl. ............ 424/248.1; 424/93.6; 424/235.1; 435/253.1; 435/866; 536/23.1; 536/23.2; 536/23.7
(58) Field of Search .................. 424/93.6, 235.1, 424/248.1; 435/253.1, 866; 536/23.1, 23.2, 23.7

(56) References Cited

FOREIGN PATENT DOCUMENTS

| WO | 90 00594 | 1/1990 |
| WO | 94 19460 | 9/1994 |
| WO | 96 33269 | 10/1996 |

OTHER PUBLICATIONS

E. Anes et al., Fems Microbiology Letters, vol. 95, 1992, pp. 21–25, XP002061610.
M.H. Lee et al., Proceedings of the National Academy of Sciences of the USA, vol. 88, Apr. 1991, pp. 3111–3115, XP002061611.
G.F. Hatfull, Trends in Microbiology, vol. 1, No. 8, Nov. 1993, pp. 310–314, XP00261612.

*Primary Examiner*—Rodney P Swartz
(74) *Attorney, Agent, or Firm*—Birch, Stewart, Kolasch & Birch, LLP

(57) ABSTRACT

The present invention discloses a DNA fragment that can direct the insertion of heterologous DNA into a specific site (tRNA$^{Ala}$ gene) of *Mycobacterium* spp. genome. This DNA fragment includes the attachment site region (attP) and the integrase gene of the mycobacteriophage Ms6. Heterologous DNA linked to this DNA fragment can be carried into the mycobacterial genome through a site-specific integration mechanism. A new DNA integration process is disclosed that consists in providing the integrase gene on a suicide vector, that transiently produces the integrase required for the insertion of the gene or genes linked to the Ms6 attP region contained in a separated plasmid vector. This process allows the construction of highly stable recombinant mycobacteria which may be used as vaccines and/or therapeutic vehicles.

12 Claims, 22 Drawing Sheets

```
  1 TCCGGCGCGG GGGGTCATCG CACGTCCTCC TCGTACCAGG CCAAGGCGAC GGGATCGCCA
 61 TCGTCGGCCC TGCGGCTGAT CTCATCGACC AGGTCGTTGA TCTTCCGCTG CCGGGAGACA
121 GCGCGGGTCG AGCCCAGCTG GCACTTCACC CAGCGACCTG CGATCCGGGC CTCGTACTCG
181 GCGATCAGAT CCGAGGTGGT GATGGTGCTC ATTTTGGAGT TCCTTTCTGT GTGCCTGATA
241 CGTCCAGAAT ACAGCACCCT CGTTACGAGT CAAGGGGTTC GGCCCCACCA ATTTCTCGTT
301 ACGTCGAAAG TCCGCGTTTC CGCACACGGG GGTGCCGCAT ATACAGGGGC GCTGTGCACA
361 GGGGTGTGGG CAGCAGCAGG GGGCTAGGGC ACAGGGGTAG GTGAGGGTGT GGGCCGCGAG
421 GGCCTCAGCC CCCCGCTCAC GCGCAACCGC CGCTCGGTAT TCAGCAGACA CCCACATGTC
                                                                  ‾
481 CGTGTTGTCA CTGACAACAC GGCTCCAGGT TTTCCCAGGT CGCTACAGGT CTAAAAAGGT
    ─────────▶ ◀─────────
541 CGGAACAGAA CCACACGGGT GTTTTTTCGC AGGTAAACGC CCATTTCCCC ACGATCGAAG
601 GGGTTCGAAT CCCCTTAGCT CCACCCAAAA CCGCAGGTCA GCGAATCGCC CAGAATCTGA
661 CAGCACCGAT GACATCACAA CGGATAGAAT CCGGGTATGG CATCAGTGCG TGAACGGGTC
                                                 M   A  S  V  R  E  R  V
721 CGCAAAGACG GAACCACCGC CTACCTGGTC TCCTACCGGT TCGGCGGCAG AGGAAGCGCA
     R  K  D   G  T  T  A   Y  L  V   S  Y  R   F  G  G  R   G  S  A
                                                                  SalI
781 CAAGGCGCAC TCACCTTCGA CAATCGCAAA GCAGCAGACG CCTTCGCCGC CGCCGTCGAC
     Q  G  A   L  T  F  D   N  R  K   A  A  D   A  F  A  A   A  V  D
841 GCCCACGGTG CTGCACGCGC CCTGGAGATG CACGGCATCA ACCCCGCACC GCGAGGAACC
     A  H  G   A  A  R  A   L  E  M   H  G  I   N  P  A  P   R  G  T
                  BamHI
901 AAGTCCGAGC TGACCGTCGC CGAATGGATC CGGCACCACA TCGACCACCT CACCGGCGTC
     K  S  E   L  T  V  A   E  W  I   R  H  H   I  D  H  L   T  G  V
961 GAGCAGTACA CGATCGACAA ATACGAGCAG TACCTCGCCA ACGACATCGA ACCCAACCTC
     E  Q  Y   T  I  D  K   Y  E  Q   Y  L  A   N  D  I  E   P  N  L
1021 GGCGACATCC CCTTGTCGAA GCTCTCCGAA GAGGACATCG CCCGCTGGGT GAAGGTCATG
      G  D  I   P  L  S  K   L  S  E   E  D  I   A  R  W  V   K  V  M
1081 GAAACCACCG GCGGCCGCGA CGGCAACGGG CACGCCCCGA AAACCCTCCG CAACAAATAC
      E  T  T   G  G  R  D   G  N  G   H  A  P   K  T  L  R   N  K  Y
1141 GGGTTCCTAT CGGGGGCACT GAACGCCGCC GTCCCCCGAT ACTTGTCCAC CAACCCTGCG
      G  F  L   S  G  A  L   N  A  A   V  P  R   Y  L  S  T   N  P  A
1201 TCGGGCCGCC GCCTGCCCCG TGGAACGCT GAGGACGACG ACGAGATCCG CATGCTCACC
      S  G  R   R  L  P  R   G  N  A   E  D  D   D  E  I  R   M  L  T
```

FIG.3A

|  | DOMAIN 1 | DOMAIN 2 |
|---|---|---|
| Int (HP1) | GLIVRICLATGARWSEAETLTQSQVMPY | HVLRHTFASHFMAKGG-NILVLKEILGHSTIEMTMR-YAH |
| Int (P22) | KSWEFALSTGLRRSNIINLEWQQIDMQ | HDLRHTWASMLVQAGV-PISVLQEMGGWESIEMVRR-YAH |
| Int (Tn1545) | YDEILILKTGLRISEFGGLTLPDLDFE | HSLRHTFCTNYANAGM-NPKALQYIMGHANIAMTLN-YYA |
| Int (Tn21) | RLFAQLLYGTGMRISEGLQLRVKDLDFD | HTLRHSFATALLRSGY-DIRTVQDLLGHSDVSTTMI-YTH |
| Int (L54a) | AGAVEVQALTGMRIGELLALQVKDVDLK | HTLRHTHISLLAEMNI-SLKAIMKRVGHRDEKTTIKVYTH |
| Int (λ) | RLAMELAVVTGQRVGDLCEMKWSDIVDG | HELR-SLSARLYEKQI-SDKFAQHLLGHKSDTMA-SQYR- |
| Int (434) | RLAMELAVVTGQRVGDLCEMKWSDIVDG | HELR-SLSARLYEKQI-SDKFAQHLLGHKSDTMA-SQYRD |
| Int (L5) | RIAAYILAWTSLRFGELIELRRKDIVDD | HDLRAVGATFAAQAGA-TTKELWARLGHTTPRWAMK-YQM |
| Int (FRAT1) | RVAVYILAWTSLRFGELIEIRRKDIMDD | HDLRAVGATLAAQAGA-TTKELWVRLGHTTPRWAMK-YQM |
| Int (Φ80) | VFLVKFIMLTGCRTAEIRLSERSMFRLD | HDWRRTIATNLSELGC-PPHVIEKLLGHQMGV-WAHYNL |
| Int (P4) | RIAVKLSLLTFVRSSELRFARMDEFDFD | HGFRTMARGALGESGLWSDDAIERQLSHSERNNVRAAYIH |
|  | *.* .. | *.* . * |
| Int (Ms6) | KLMVQFMVSTGLRWGEVSALQPRHVDLE | HDLRHTYASWQLTGGT-PVTIVSRQLGHESIQITVDTYTD |

The alignment was done on 12 Protein sequences.
Character to show that a position in the alignment is perfectly conserved: '*'
Character to show that a position is well conserved: '.'

FIG.4 tRNA^ALA of *Mycobacterium smegmatis* tRNA^ALA gene sequences:

*Mycobacterium tuberculosis* H37rv
5' GGGGCTATGGCGCAGCTGGTAGCGCACCACACTGGCAGTGTGGGGGTCA<u>GGGGTTCGAGTCCCCTTAG CTCCAC</u> 3'

*Mycobacterium smegmatis*
5' GGGGCTATGGCGCAGTTGGTAGCGCACCACACTGGCAGTGTGGGGGTCA<u>GGGGTTCGAATCCCCTTAG CTCCAC</u> 3'

5' GAT CGCCTTGTCC AACACCCCCG AGTTCACGTT GAACGCCACC GAAACCATCA
    ‾‾‾‾
    Sau3A

CCCAGGTGTC GTTCTGGACC GAGGCCACCG GCGGGTATT CCTGGCCTCA GCAGCAGCCT

CGGTGGCCAA AGGCGGCGTG TCCGGGGACA TCATCCGGCAT CCAGACGGCA CCCATCTCCT

TCACCGGACT CGGGGCCTGA TGTCCGACCA CCCCGACAAC TACACTATCC TCGGTATCGA

AAAACCTTTC CCCTGGATC 3'
              ‾‾‾‾
              Sau3A

Sau3AI DNA fragment of 252 bp which encodes the promoter P1.

FIG.17

```
Primer pm4 →                           Term. transcr. fago T4
CCTTTAATAG ATTATATTAC TAATTAATTG GGGACCCTAG AGGTCCCCTT TTTAAAAATT TTTTCACAAA
                                ScaI ApaI SacI

ACGGTTTACA AGCATAAAGC TAGTACTGGG CCCGCGGATC GCCTTGTGTCCA ACACCCCGA GTTCACGTTG

AACGCCACCG AAACCATCAC CCACGTGTCG TTCTGGACCG ACGCCACCGG CGGGTATTC CTCGCCCTCAG

CAGCAGCCTC GGTCGCCAAA GCGGGCGTGT CCGGGGACAT CATCCGCATC CAGACGCGCAC CCATCTCCTT

CACCGGACTC GCGGCCTGAT GTCCGACCAC CCCGACAACT ACACTATCCT CGGTATCGAA AAACCTTTCC
                  SphI KpnI  HindIII*                   SD                    cII

CCTGGATCCG CATGCGGTAC CAAGCTTGAT CCGATAACAC AGGAACAGAT CTATGGTTCG TGCAAACAAA

CGCAAGGAGG CTCTACGAAT CGGAAGCTTC GATCCCGTCG TTTTACAACG TCGTGACTGG
    ← Primer pm2
```

FIG.19

DNA INTEGRATION INTO "MYCOBACTERIUM SPP." GENOME BY TRANS-COMPLEMENTATION USING A SITE-SPECIFIC INTEGRATION SYSTEM

This application is the national phase under 35 U.S.C. §371 of PCT International Application No. PCT/PT97/00005 which has an International filing date of Aug. 6, 1997 which designated the United States of America.

BACKGROUND

Mycobacteria is a major bacterial pathogen group for man in which are included the etiological agents of tuberculosis and leprosy, respectively Mycobacterium tuberculosis and Mycobacterium leprae. Mycobacterium tuberculosis accounts for more deaths world wide than any other human pathogen. The World Heath Organization estimated that there are approximately 8 million new cases and an annual mortality of 3 million. On the other hand leprosy afflicts 10 to 12 million people in 152 countries. Leprosy is endemic in the Arctic Circle and in Africa, South-America and South-East Asia. M. bovis and M. africanum can also cause tuberculosis in humans. M. bovis causes tuberculosis in ruminants and in other animals and can be transmitted to humans by ingestion of contaminated milk or meat. Tuberculosis associated with M. africanum has been diagnosed in immigrants from Central African countries.

Many species of mycobacteria other than M.tuberculosis, M. africanum, M. bovis and M. leprae present in the environment can also cause human diseases. For example, pulmonary diseases may be caused by the M. kansasii, M. xenopi and M.avium complex. M. marinum, often isolated from aquaria and swimming pools, may cause chronic granulomas of the skin.

On the other hand BCG, an avirulent strain of M. bovis, is widely used as a vaccine against tuberculosis. This bacillus was developed by Calmette and Guérin who noted a change in colony morphology after a serial passage of a virulent strain of M. bovis in a potato glycerin medium containing ox bile. The efficacy of BCG continues to be debated. BCG protects against serious and disseminated disease including meningitis in newborn babies. However, its efficiency to prevent pulmonary forms, particularly in adults, was shown to be variable.

The main advantage of live vaccines is that they can persist in the host owing to their capacity to replicate, resulting in continuous exposure of the host to the vaccine antigen. Thus, it is possible that a single dose of live vaccine could represent an effective dose for the induction of a long-lasting immune response. A vast array of bacterial species have been attenuated by a variety of means in an attempt to develop both safe and effective vaccines and carrier strains for heterologous vaccine antigens. The BCG is the only bacterial live vaccine that has been extensively used in humans. In the past 40 years it has been administered to more than 2.5 billion people with very few adverse effects. BCG offers some other unique attributes for the development of live vaccine vehicles: 1. it can be given at birth or shortly after; 2. it is able to induce a long-lasting immune response; 3. it is a potent immunological adjuvant; 4. BCG can be administrated as an oral vaccine to stimulate mucosal immunity; 5. it is heat stable; BCG does not require conservation at low temperatures; 6. it is easy and inexpensive to produce.

The development of genetic tools for mycobacteria has enabled the cloning and the expression of foreign genes in fast-growing M. smegmatis mycobacteria and in M. bovis BCG. Plasmids have been identified in several species of mycobacteria such as M. avium, M. scrofulaceum and M. fortuitum, though the functions of most of them are unknown. The most thoroughly studied mycobacterial plasmid was the cryptic plasmid pAL5000 isolated from a strain of M.fortuitum by Labidi and co-workers 1984. The analysis of the complete sequence of the pAL5000 revealed 5 ORF and an origin of replication (Rauzier, J., Moniz-Pereira, J., and Gicquel, B. Gene 71:315–321, (1988)). This information was essential for the construction of small shuttle vectors for E.coli mycobacteria, which include an origin of replication functional in E. coli (OriE) derived from pUC19. As a genetic marker the Tn903-derived aph gene was used, which confers kanamycin resistance to the transformants. Expression cassettes derived from the promoter regions of BCG hsp-60 (Thole, et al., Infect. and Immun., Vol.55, p.1466–1475 (1987)) and hsp-70 (Young, R.) genes ( M.tuberculosis 19-kDa antigen (Ashbridge, K. R et al., Nucleic Acids Res. Vol. 17: 1249.1989. Stover, K. et al., J. Exp. Med., Vol 178: 197–209. (1993)), M. fortuitum bla gene (Timm, J. et al., Mol.Microbiol. Vol. 12: 491–504. (1994)) among others, were successfully used for the expression of foreign genes in fast-growing mycobacteria and in BCG.

The use of recombinant mycobacteria as multivalent vaccine vehicles requires a stable construction for a long expression of the antigen genes following the administration of the bacteria to the host.

Antigenic-expressing plasmid vectors are not very stable in the absence of selection, although they reach high levels of expression of the foreign DNA.

One of the possibilities for increasing the stability of recombinant bacterial strains is to use a site-specific integration system of temperate bacteriophages. By this process a heterologous DNA covalently linked to a phage DNA integration locus can be inserted into the bacterial genome and be maintained for a long time.

The temperate mycobacteriophage Ms6, isolated from the strain of Mycobacterium smegmatis HB5688, is able to infect and to lysogenize some strains of M. smegmatis. It was shown that Ms6 can be used as a vehicle for the insertion of foreign DNA into mycobacteria genome. The aminoglycoside phosphotransferase gene from the Tn5 transposal was inserted into the M. smegmatis genome through lysogenization using a transducing derivative of the mycobacteriophage Ms6. It was demonstrated that Ms6 DNA can be inserted into the bacterial genome through a site-specific recombination mechanism. The DNA restriction fragment that contains the phage attachment site attP was identified and sequence analysis of this region showed that Ms6 is different from D29 and L5 mycobacteriophages. The integrative locus of mycobacteriophage Ms6 was sequenced and inserted into a plasmid vector. This recombinant plasmid was integrated into Mycobacterium smegmatis, M. bovis-BCG, M tuberculosis. The present invention was based on the site-specific integration system of the mycobacteriophage Ms6.

SUMMARY OF THE INVENTION

The object of the present invention is the construction of highly stable recombinant mycobacteria strains, particularly BCG, to be used as "in vivo" vectors for presenting antigens, immunomodulators and other therapeutic agents.

The present invention relates to: 1. the Ms6 DNA integrating region responsible for the integration of the bacteriophage DNA into the mycobacterial genome; 2. a second DNA fragment that includes the Ms6 attP region linked to an expression cassette composed of the relevant DNA sequence (which may encode a variety of heterologous genes, including genes for antigens which protect against several pathogens, lymphocynes and other therapeutic agents) under the control of a promoter region; 3. a third DNA fragment that carries the integrase gene under the control of a strong promoter region originating from the bacteriophage Ms6; 4. a new method of integrating DNA based on the transient production of integrase sufficient for directing the integration of the relevant DNA sequence linked to the attP region into the bacterial genome; 5. the expression of vaccine-stable vehicles which are such recombinant strains of mycobacteria produced by this new integrating process capable of continuously expressing the relevant DNA fragment.

The Ms6 DNA integrating region (attP-int) includes: the phage attachment site (attP) with the bacterial genome and the gene of the integrase, which encodes the enzyme that mediates the recombination between the attP and a corresponding attB site of the bacterial genome. This mechanism is called site-specific integration because it only occurs in a particular site of the bacterial genome. A common core sequence is present in both the attP and attB regions and is the site where the DNA exchange occurs. This recombinational event leads to the duplication of the common core sequence which will flank the inserted DNA.

The DNA integration process of the subject invention has important advantages over the integrating systems that are presently available. In particular, an improvement of the transformation efficiency of mycobacteria due to the use of a bacteriophage integrase in the integration process. This differs from the process that is presently available in which the DNA fragment is integrated into the bacterial genome by a double homologous recombination mechanism which, in slow growing bacteria such as BCG, occurs with a very low frequency, resulting in poor transformation efficiency.

An integrative vector based on a mycobacteriophage attP-int region linked to an expression cassette is available to construct recombinant mycobacteria strains. However, considering that in bacterial lysogens the excision process of the prophage requires the contribution of the integrase and the excisionase, it is possible to improve the stability of the recombinant strains by eliminating the integrase gene from the integrative vector. This is the subject of the present invention. A new process is proposed which eliminates the integrase gene from the integrative vector and therefore from the genome of the recombinant mycobacteria produced to guarantee the stability of the recombinant strains. This novel integration process consists in transforming the mycobacterial cells simultaneously with two plasmids. Plasmid 1 includes the integrase gene under the control of a strong promoter region and it is not capable of replication because it does not have a mycobacterial origin of replication. Plasmid 2 contains the attP region linked to a relevant DNA which is under the control of mycobacterial gene regulation signals. The supply of the integrase gene in an independent suicide vector produces enough integrase to direct the integration of plasmid 2 which carries the attP region and the relevant DNA.

It was confirmed that this process of integrating relevant DNA into the bacterial genome produces recombinant mycobacterial strains that do not lose the exogenous DNA following long non-selective growth. Therefore, these highly stable recombinant mycobacterial strains can be safely used as vehicles to express, following administration to humans or animals, a gene or genes of interest. These recombinant mycobacterial strains can be used as vectors for presenting one or more protective antigens, against one or more pathogenic agents. These mycobacterial vehicles can also be used to express immunopotentiators, cytosines, anti-tumour and anti-cancerous agents and other useful polypeptides and proteins.

The integrative vectors and the integrating process described in this invention have made it possible to insert exogenous DNA into the genome of a wide range of Mycobacterium species, including: *M.smegmatis, M.vaccae, M. tuberculosis, M. bovis*-BCG.The scope of the present invention is not restricted to mycobacteria and is applicable to other bacteria, such as: Salmonella ssp., Vibrio spp., Shigella spp., Lactobacillus spp., Streptomyces spp., Corynebacterium spp., Listeria spp.

BRIEF DESCRIPTION OF THE DRAWINGS

FIG. 4: Identification of the Ms6 integrase from amino acid sequence similarity of the C-terminal region with λ-Int related integrases. Two of the more conserved integrase domains are shown. The second domain includes the histidine, arginine and tyrosine residues characteristically shared by all members of the integrase family. The Ms6 intregrase is a member of the λ related integrases. The perfectly conserved amino acids are indicated by an asterisk and highly conserved amino acids by dots.

FIG. 17: DNA sequence of the 252 bp Sau3AI DNA fragment that encodes the Ms6 promoter P1 (SEQ ID NO: 52).

FIG. 19: DNA sequence of the expression cassette P1-CII-LacZ. This DNA fragment was isolated from plasmid pMG1 by PCR using primer pm4 (SEQ ID NO: 14) and primer pm2 (SEQ ID NO: 15). Plasmid pMG1 resulted from the cloning of the Ms6 252 bp Sau3AI fragment that encodes for promoter P1 (SEQ ID NO: 52) into the BamHI site of the promoter probe plasmid pJEM.15 (J. Timm et al. 1994, J. Bacteriol. Vol. 176; 6749–53).

DETAILED DESCRIPTION OF THE INVENTION

The invention will now be described with the respect to the following examples. However, the scope of the present invention is not limited thereby.

EXAMPLE 1

A. Identification of the attP-int Region of the Mycobacteriophage Ms6 DNA

Figure 1:
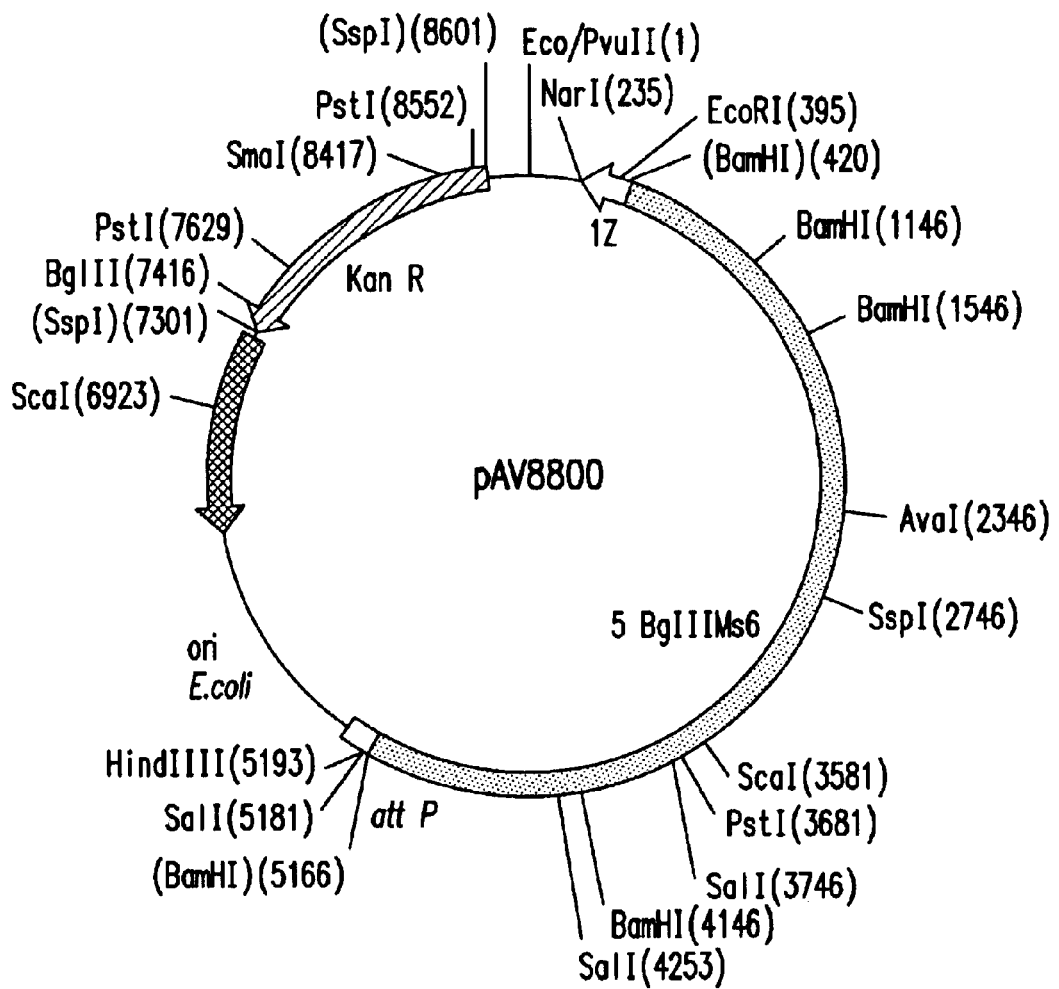
FIG. 1: Map of plasmid pAV8800. The 4.8 kb BglII restriction fragment of mycobacteriophage Ms6 was inserted into the single site BamHI of plasmid pZM4. pZM3 is a derivative of the pUC19 (Yanisch-Perron, C., Vieira, J. and Messing, J. (1985) Gene 33, 103–119) where the aminoglycoside phosphotransferase gene (aph) from Tn5 was inserted between the sites ScaI and SspI.

The site-specific integration locus of the mycobacteriophage Ms6 DNA was previously pinpointed to a 4.8-kb BglII restriction fragment. This fragment was cloned in a pUC19-derived plasmid vector and the recombinant plasmid generated was named pAV8800 (FIG. 1) and electroporated into *M. smegmatis*. The DNA of the transformants was analyzed by the Southern/hybridization method in order to test the integration of the recombinant plasmid. In all the transform ants analyzed the same pattern of bands was found, indicating a site-specific integration mechanism.

Figure 2:
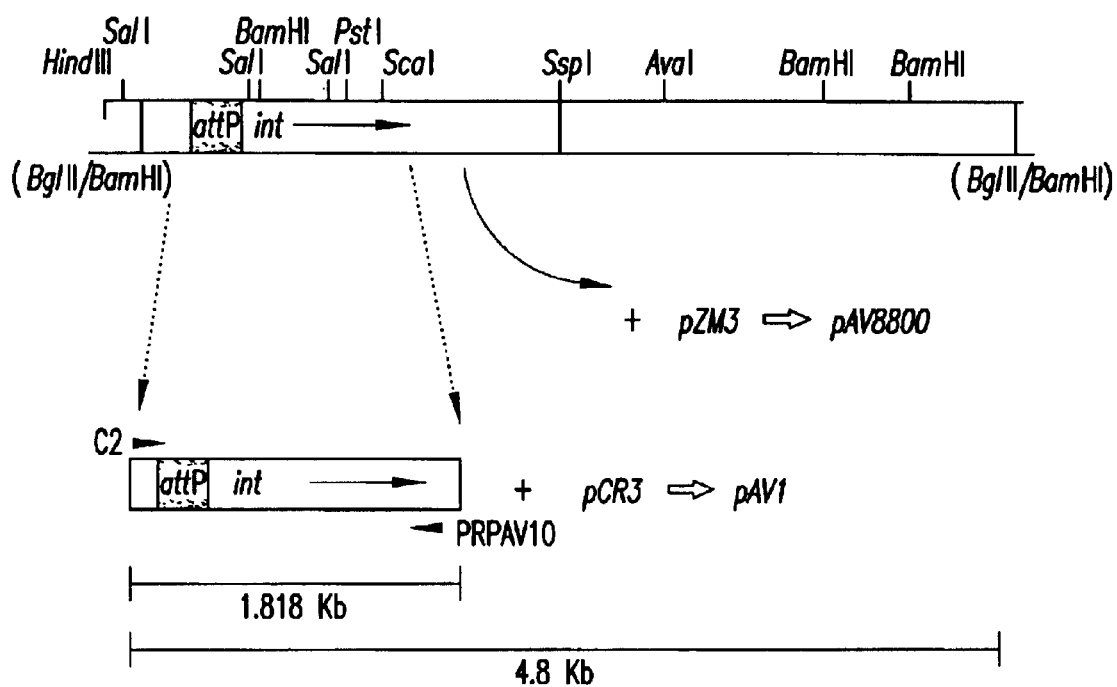
FIG. 2: Restriction map of the 4.8 kb BglII of mycobacteriophage Ms6 fragment is outlined. The location and translational direction of the int gene are represented as an arrow on the right of the attP site. C2 (SEQ ID NO: 3) and PRPAV10 (SEQ ID NO: 4) are primers designed for PCR amplification of the attP-int region.
Figure 3B:
FIG. 3: DNA sequence of the 2.4-kb BglII-SspI restriction fragment that contains the Ms6 attP-int region (SEQ ID NO: 16). The amino acid sequences deduced from the int gene are given below the nucleotide sequence. Relevant restriction sites are indicated. The core sequence of the attP site is boxed. Primers C2 (SEQ ID NO: 3) and PRPAV10 (SEQ ID NO: 4) are underlined. Opposed arrows indicate the positions of the inverted repeats. (GenBank database under the accession number AF030986).

The attP phage attachment region was located in a 0.8-kb BglII-SalI fragment at the far left of the 4.8 kb BglII fragment (Anes, et al., 1997) (FIG. 2). Considering that in the majority of the procaryotic site-specific integration systems the integrase (int) gene is close to the attP, the DNA stretch between BglII and SspI that contains the Ms6 attP region was sequenced (FIG. 3) (SEQ ID NO:16 (DNA) and SEQ ID NO:17 (amino acid)). The base composition of this region is 63% G+C, which is practically identical to other mycobacterial genetic elements.

An ORF of 1119 bp starting in an ATG initiation codon at the position 697 and ending in a stop codon at the position 1815 was identified. The deduced protein of 372 amino acids was aligned with other integrases (FIG. 4). Although integrases have poor homology among their amino acid sequences, the carboxy-terminal regions contain amino acids which remain in specific positions. The alignment revealed the presence of an arginine in the middle of the first domain, as well as the histidine, arginine and tyrosine residues in the second domain, which is a characteristic shared by all members of the integrase family In FIG. 4, Sequence Identification Numbers are as follows: For Domain 1, Int(HP1) SEQ ID NO:18; Int (P22) SEQ ID NO:20; Int (Tn 1545)=SEQ ID NO:22; Int (Tn21)=SEQ ID NO:24; Int (L54a)=SEQ ID NO:26; Int (λ)=SEQ ID NO:28; Int (434)=SEQ ID NO:30; Int (L5)=SEQ ID NO:32; Int (FRAT1)=SEQ ID NO:34; Int (Φ80)=SEQ ID NO:36; Int (P4)=SEQ ID NO:38; Int (Ms6)=SEQ ID NO:40. For Domain 2, Int(HP1)=SEQID NO:19; Int (P22)=SEQ ID NO:21; Int (Tn 1545)=SEQ ID NO:23; Int (Tn21)=SEQ ID NO:25; Int (L54a)=SEQ ID NO:27; Int (λ)=SEQ ID NO:29; Int (434)=SEQ ID NO:31; Int (L5)=SEQ ID NO:33; Int (FRAT1)=SEQ ID NO:35; Int (Φ80)=SEQ ID NO:37; Int (P4)=SEQ ID NO:39; Int (Ms6)=SEQ ID NO:41.

This observation shows that this ORF encodes the integrase of the bacteriophage Ms6. A threonine residue in the first domain is also present in all the integrase sequences represented in FIG. 4, whereas this characteristic is absent in some bacteriophage integrase-related proteins.

The attP-int region of Ms6 DNA is limited by two inverted repeat sequences. At the 3' terminus of the int gene lies a structure resembling a rho-independent transcriptional terminator that can form a hairpin secondary structure followed by a poly T-rich sequence. At the 480 position (FIG. 3) a second inverted repeat is located which can form a 10-bp stem loop, but no poly T-rich sequence is present close to it. Preliminary functional experiments showed that this inverted repeat is required for integration. As in other integration systems, this inverted repeat may belong to the attP region and may be a site that is recognized by the integrase.

B. Identification of the DNA Sequences of the Phage and Bacterial Attachment Sites The common sequence where the recombination between the phage DNA and the bacterial genome occurs was determined after the alignment of 4 DNA fragments: 1–2) the right and the left host-phage DNA junctions (attR (SEQ ID NO:44) and attL (SEQ ID NO:43)), 3) the bacteriophage attP-int (SEQ ID NO:42) region and 4) the attachment site in the bacterial genome attB (SEQ ID NO:45) (FIG. 5).

To identify the host-phage DNA junctions, a λEMBL4 library was constructed by molecularly cloning the genome of an M. smegmatis (pAV8800) transformant. A recombinant phage containing the complete pAV8800 sequence, inserted within an EcoRI bacterial restriction fragment, was analysed by Southern/hybridization using a 0.8-kb BglII-SalI fragment which contains the phage attachment region, as a probe. Two SalI restriction fragments with respectively 0.9 kb and 1.2 kb containing the putative attR and attL sites were identified and sequenced. The attB region was directly amplified by PCR from the M. smegmatis DNA, using specific oligonucleotides p1 (5'-CGCTGTTGGTGGGCCTGATCG-3') (SEQ ID NO:1) and m1 (5'-ACACGCCGGATGAATGACC-3') (SEQ ID NO:2) designed from the right and left junction sequences.

Figure 5:
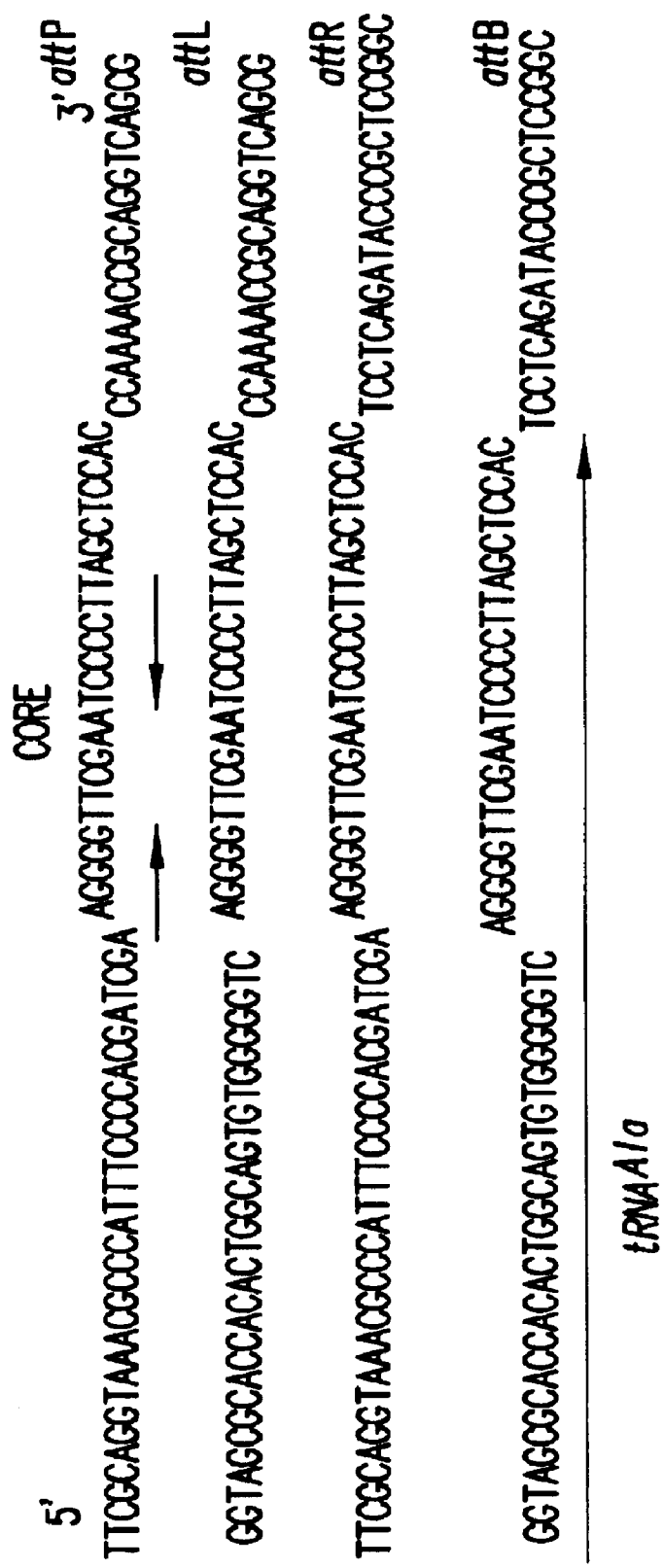
FIG. 5: Alignment of the DNA sequences of attP(SEQ ID NO: 42), attR (SEQ ID NO: 44), attL (SEQ ID NO: 43) and attB (SEQ ID NO: 45) showing a common core sequence of 26 bp. The position of the tRNA$^{Ala}$ gene is represented by the arrow below the attB sequence.

The alignment of the attR, attL, bacteriophage attP region and attB sequences revealed a 26 bp common core sequence where the recombination between the phage DNA and the bacterial genome occurs (FIG. 5).

C. Identification of the Bacterial Genome Region where the attB Sequence is Situated In M. smegmatis genome the common core region lies at the 3' end of a sequence (SEQ ID NO:47) that has 83.8% homology with the tRNA$^{Ala}$ gene of Micrococcus luteus and 76% with the tRNA$^{Ala}$ gene of E.coli. Moreover, this target sequence possesses, as do all the tRNA$^{Ala}$ genes studied to date, a characteristic base pair (G3-U70) in the amino acid acceptor stem of the tRNA structure (FIG. 6 (SEQ ID NO:46)), (19). These observations indicate that in lysogenic strains Ms6 DNA is inserted at the 3' terminal sequence of the M. smegmatis tRNA gene.

Figure 6:
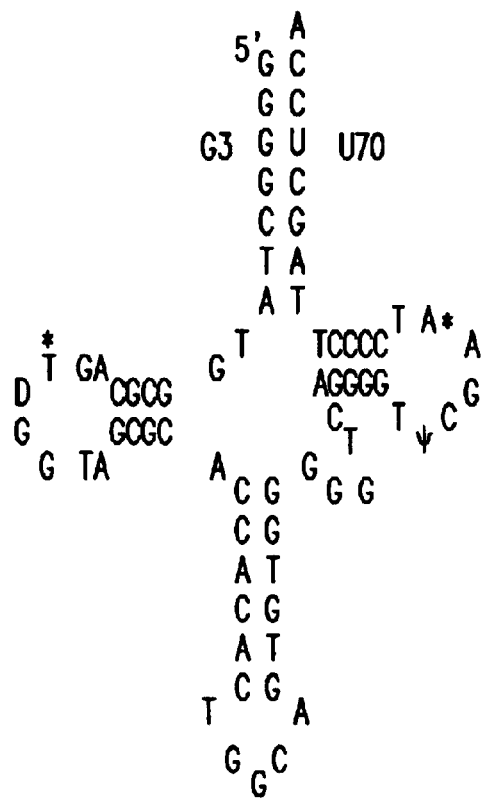
FIG. 6: Alanine tRNA encoded by *M. smegmatis* attB region. The folded structure of the alanine tRNA is shown (SEQ ID NO: 46).

The common core sequence is also found in the cosmid cSCY22D7 of the genome library of M.tuberculosis H37Rv supplied by Dr. Stewart Cole and his colleagues at the Institut Pasteur and it has been sequenced by the Sanger Center. The sequence analysis of the homologous segment in the M. tuberculosis genome (SEQ ID NO:48) indicates that both tRNA genes are present within a similar organization. However, there are two altered bases which lie within the D loop (a T to C change in M. tuberculosis) and the TΨGC loop (G instead of A) as shown in FIG. 6. Nevertheless, this G to A change within the core region does not appear to have any significant effect on the efficiency of integration as determined by the transformation frequencies.

D. Construction of the Integrative shuttle Vector pAV1

The 4.8 kb BglII restriction fragment which encodes the integrative functions of the mycobacteriophage Ms6 was cloned into the pUC19 derived plasmid, pZM3, which carries the aph gene that confers resistance to Tn5 kanamycin. The new plasmid named pAV8800 (FIG. 1) was electroporated into M. smegmatis, M.vaccae and BCG. The results of the transformation efficiency expressed as the number of kanamycin-resistant transformants per μg of DNA are shown in Table 1.

The stability of the M. smegmatis recombinants produced was tested. After growth in a non-selective medium for 50 generations, 95% of the clones remained kanamycin-resistant. However, none of the 4 BCG recombinants obtained survived new cultures in selective or non-selective media.

Southern/hybridization studies confirmed that the plasmid sequences are integrated in a specific site of the bacterial genome in all the M.smegmatis transformants analyzed.

In order to improve the stability of the recombinant mycobacteria and, on the other hand, to demonstrate that the attP sequence and the int gene are sufficient for directing site-specific integration into the mycobacteria genom, the attP-int region was produced by PCR directly from Ms6 DNA. Using the initiating sequences C2 (5'-

Figure 7:
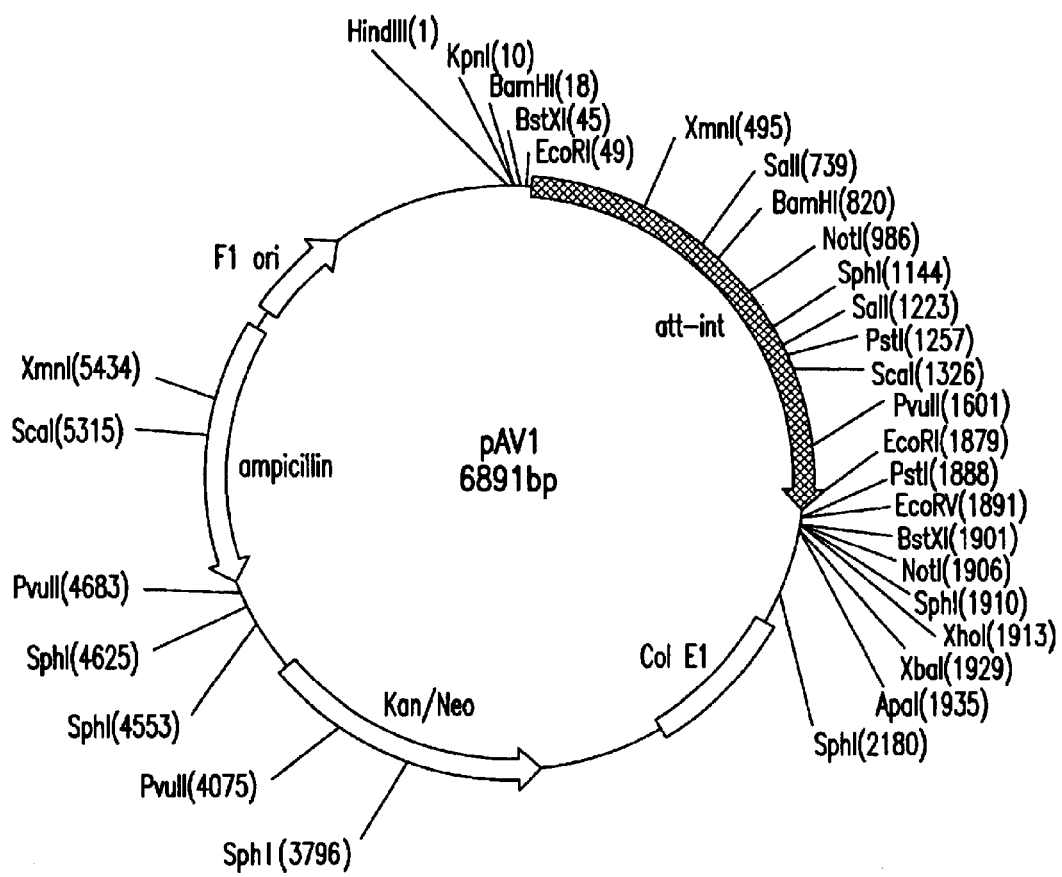
FIG. 7: Map of plasmid pAV1. pAV1 was constructed by inserting a fragment containing the attP-int region, obtained by PCR from the Ms6 DNA using primers C2 (SEQ ID NO: 3) and PRPAV10 (SEQ ID NO: 4), in plasmid pCR3 (Invitrogen).

GATCCGGGCCTCGTACTCG-3') (SEQ ID NO:3) and PRPVA10 (5'-CAACCCGACGGTGTTGCG-3') (SEQ ID NO:4) a fragment of 1818 bp containing the integrative functions was produced and was then cloned in the plasmid vector pCR3 (invitrogen). The recombinant plasmid produced, pAV1 (FIG. 7), replicates extrachromosomally in *E.coli* but not in mycobacterial cells because it does not contain any mycobacterial origin of replication. pAV1 was electroporated into *M. smegmatis, M. vaccae*, BCG, *M. tuberculosis* H37Ra. The electroporation process used in all the experiments described in this invention was carried out as follows: mycobacterial cells were grown in 500 ml of Myco Broth (Middlebrock 7H9, Nutrient Broth of Difco, 0.5% glucose and 0.05% Tween 80) to $OD_{600}$ 0.8, harvested by centrifugation, washed 3 times with 500 ml of cold 10% glycerol and finally resuspended in 2 ml of cold 10% glycerol. 1 µl of DNA was added to 40 µl of cells in an ice-tray with a 0.1 cm gap between the electrodes and pulsed in a Bio-Rad Gene Pulser device. A single pulse at 1.8 kV and 25 µF was given with the Pulse Controller resistance at 200 Ohms. The samples were diluted in 5 ml of broth and incubated for 1 hour at 37° C. for expression of the antibiotic-resistant gene. Cells were concentrated and plated on a Myco agar (Myco Broth with 1.2% of Bacto Agar) medium containing 15 µg/ml of kanamycin.

The number of transformants per µg of DNA was respectively $10 \times 1.0^5$ and $3 \times 10^3$ in *M. smegmatis* and BCG/*M.tuberculosis* (Table 1). These transformation efficiency values are similar to those obtained with pRR3 (Ranes, M. G., J. Rauzier, M. Lagranderie, M. Gheorghiu, and B. Gicquel, J. Bacteriol. vol. 172:2793–2797.1990), a shuttle plasmid that replicates extrachromosomally in Mycobacterrium spp and *E. coli*.

TABLE 1

Transformation efficiency of Ms6-derived integrative vectors

| Stain | Transformants/µg of DNA | | |
|---|---|---|---|
| | pAV8800 | pAV1 | pRR3 |
| *M. smegmatis* mc²155 | $1.3 \times 10^4$ | $1.0 \times 10^5$ | $>10^5$ |
| *M. vaccae* | $1.2 \times 10^4$ | ND | ND |
| BCG Pasteur | 4 | $4 \times 10^3$ | $4 \times 10^3$ |
| *M. tuberculosis* H37Ra | ND* | $3 \times 10^3$ | $4 \times 10^3$ |

*ND - Not done

The plasmid pAV8800 which contains 4.8 kb BglII gives a lower number of transformants ($1.3 \times 10^4$) in the mc² 155 strain than pAV1 ($1.0 \times 10^5$). In BCG the difference in the transformation efficiency between these two plasmids is bigger, 3 logs. The explanation for this behaviour has not yet been found, although the answer can be obtained when the functions encoded in the DNA segment at the 3' end of the attP-int region were revealed.

Disruption of the ORF present in the Ms6 integrative region destroys the ability to transform mycobacteria. The deletions and insertions performed at the 3' end of the int gene lead to non-integrative activity.

Figure 8A:
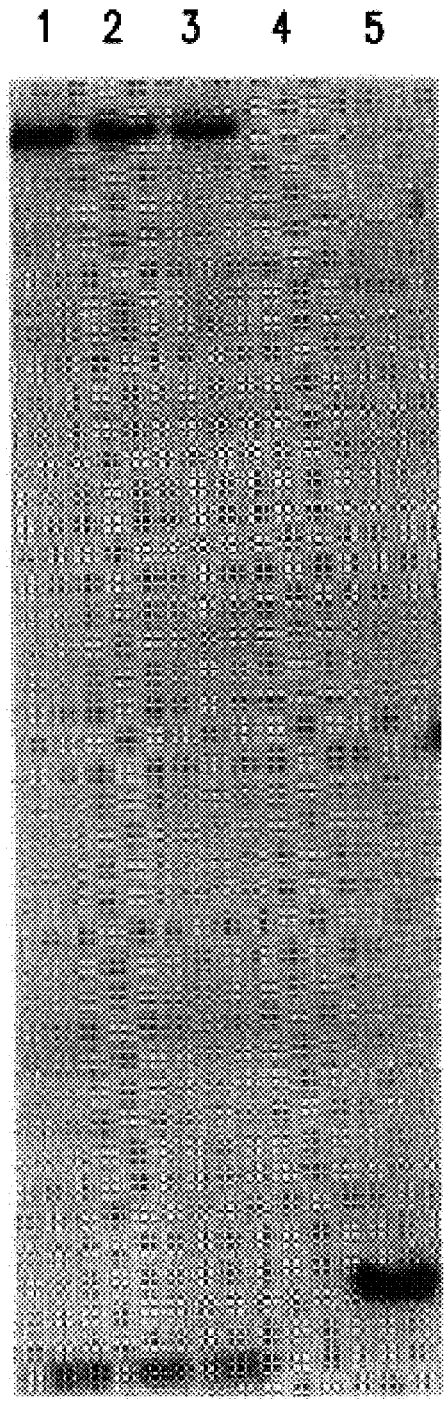
FIG. 8: Southern hybridization analysis of *M. smegmatis* pAV1 transformants. Three independently isolated pAV1 transformants (lanes 1 to 3), chromosomal DNA from *M. smegmatis* (lane 4) and pAV1 (lane 5) were digested with BamHI and probed with the 0.8 kb SalI attP fragment (a) or with *M. smegmatis* attB region (b).
Figure 8B:
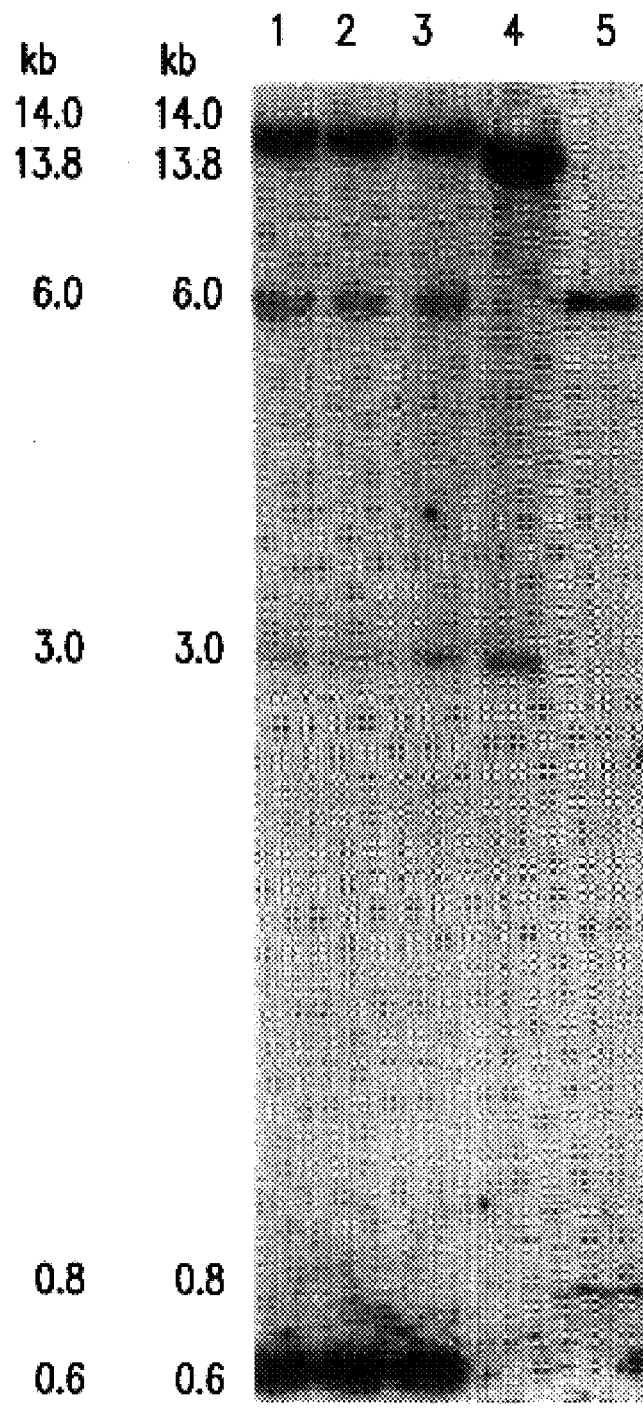
Figure 9A:
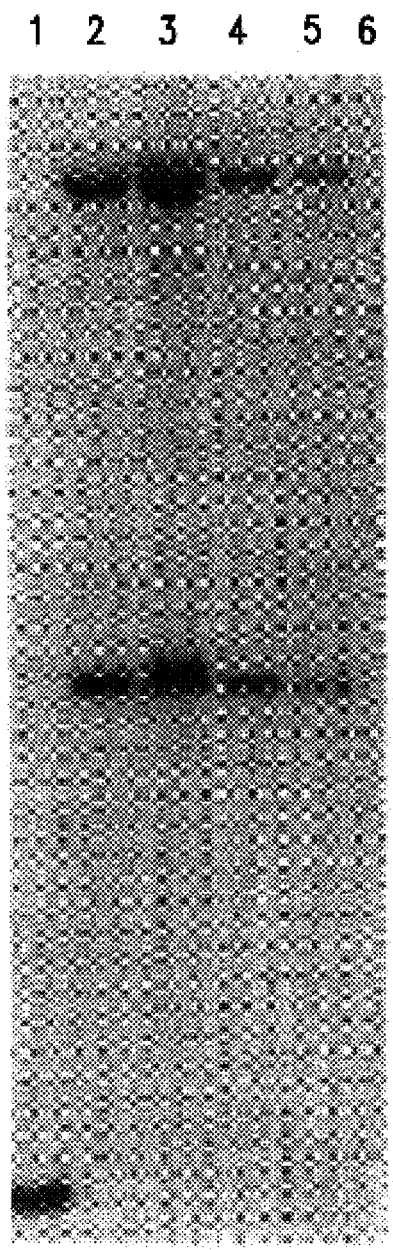
FIG. 9: Southern hybridization of BamHI-digested chromosomal DNAs of BCG and *M. tuberculosis* pAV1 transformants. BamHI digested pAV1 (lane 1), four independently BCG transformants (lanes 2 to 5) and BCG Pasteur genomic DNA (lane 6) were probed with the 0.8 kb SalI attP fragment (a) or with *M. smegmatis* attB DNA(b).
Figure 9B:
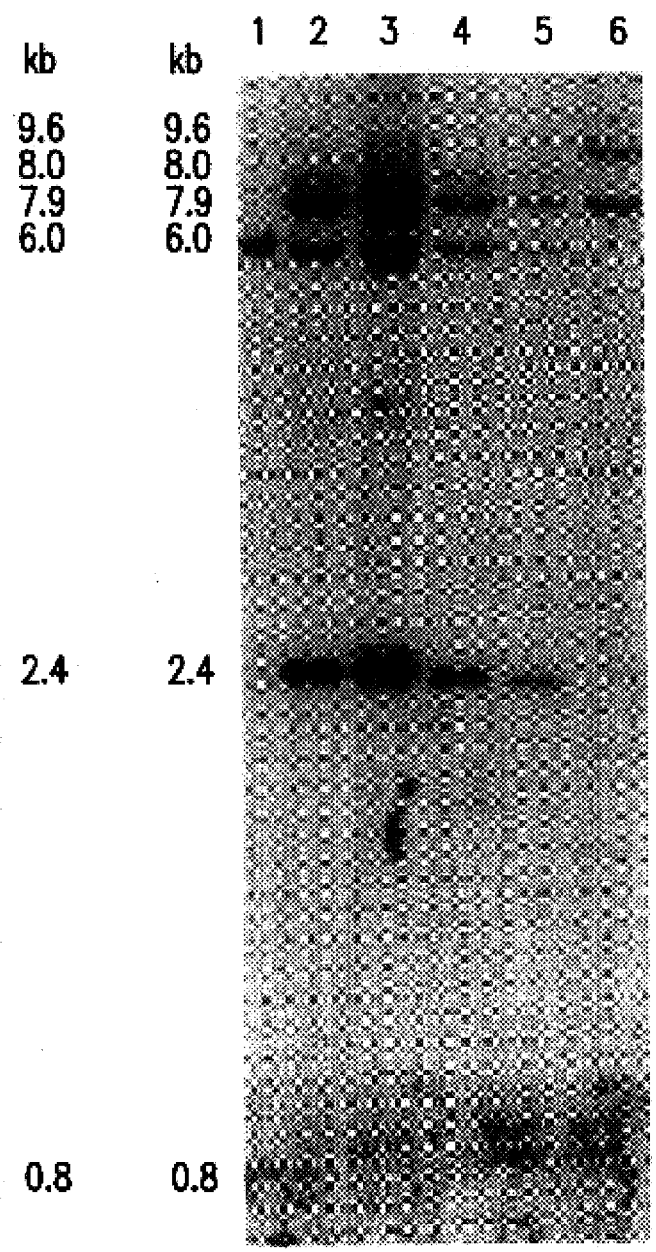
Figure 10:
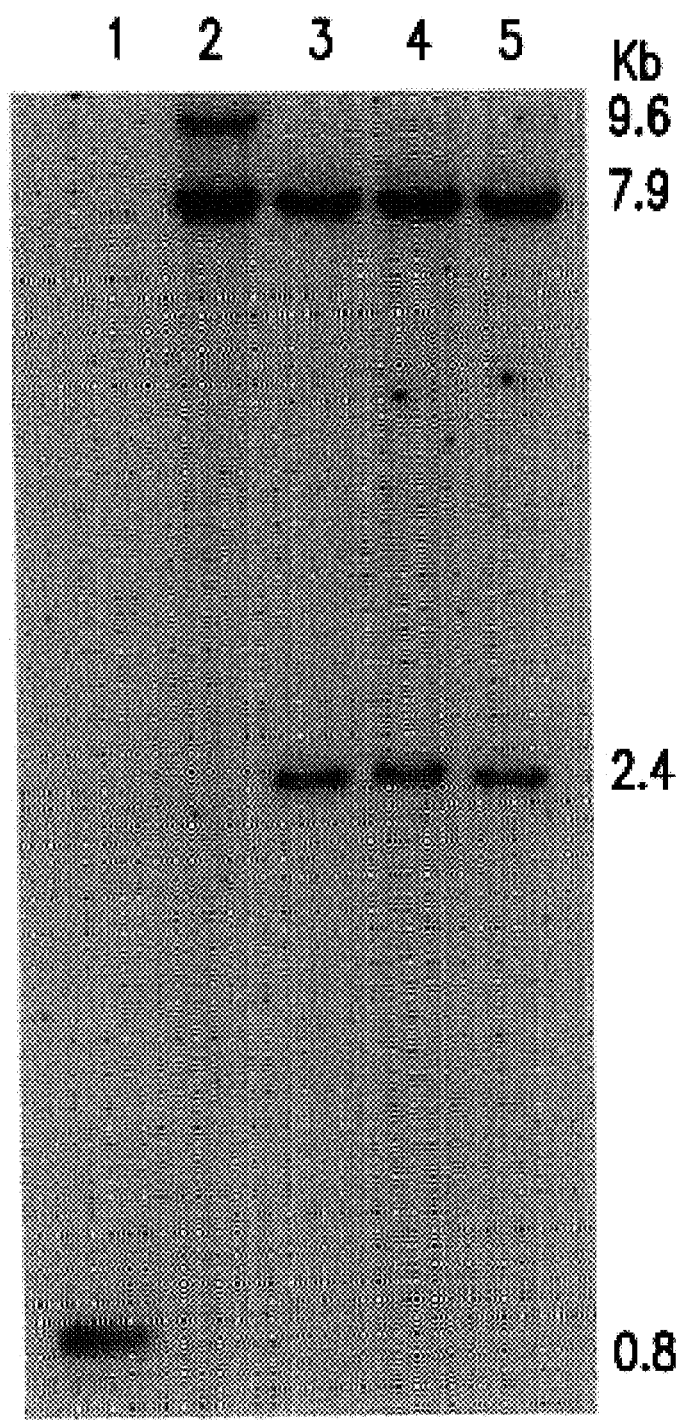
FIG. 10: Southern hybridization of BamHI-digested chromosomal DNAs of BCG and *M. tuberculosis* pAV1 transformants. BamHI-digested pAV1 (lane 1), three *M. tuberculosis* pAV1 transformants, (lanes 3 to 5) and *M. tuberculosis* H37Ra genome (lane 2) were probed with *M. smegmatis* attB DNA.

Southern/hybridization analysis confirmed that the Ms6-derived integrative plasmid (pAV1) was inserted into the same site (attB) in all transformants examined (FIG. 8). Chromosomal DNA from three independent $Km^R$ transformants and from pAV1 were cut with BamHI and hybridized with the radiolabelled Ms6 attP region. This probe did not hybridize with chromosomal DNA from *M. smegmatis* (FIG. 8A, lane 4), while two hybridizing bands of 14 kb and 0.6 kb respectively were visualized in the chromosomal digests of all the $Km^R$ transformants (FIG. 8A lanes 1, 2 and 3). The 0.8 kb BamHI restriction fragment, derived from pAV1, containing the attP region, is intact in lane 5. In FIG. 8B hybridization with the attB probe (a 0.5 kb DNA segment *M. smegmatis*, obtained by PCR and cloned into pCR3) revealed a 13.8 kb fragment in the *M.smegmatis* DNA digests (lane 4), which is absent in all transformants. In turn, in these digests the two hybrid fragrnents (14 kb and 0.6 kb) were detected (lanes 1, 2 and 3). The sizes of the two hybridizing bands were consistent with the prediction for integration of a pAV1 copy into the *M.smegmatis* genome at the attachment site (attB) present in the 13.8 kb BamHI fragment (FIG. 8B, lane 4). The 6 kb restriction band in FIG. 8B corresponds to common sequences present in both pCR3 and pAV1 plasmids. The 3 kb fragment found in all *M.smegmatis* DNA digests possibly corresponds to another region that contains sequences with high homology with this probe.

pAV1 was also stably integrated, by a site-specific integration mechanism, in the BCG (FIGS. 9A and B) and *M. tuberculosis* H37Ra genomes (FIG. 10). In these slow-growing mycobacteria the plasmid integration target hybridizes with the *M.smegmatis* attB sequence. However, the sequences that are linked to the $tRNA^{Ala}$ gene of *M. tuberculosis* are completely different from those of *M. smegmatis*. As a consequence of this, only one hybrid band with 2.4 kb (FIG. 10, lanes 3, 4 and 5) can be detected by Southern/hybridization analysis of the DNA of H37Rv transformants using the attB region of *M.smegmatis* as a probe. It can be concluded that the pAV1 integration site in the genome of the fast and slow-growing mycobacteria consists of the last 25 bases of the $tRNA^{Ala}$ gene (FIG. 6).

E. Stability of the Recombinant Mycobacteria

The stability of the *M. smegmatis* transformants carrying a plasmid inserted in their genome was evaluated as follows: The recombinant cells were grown to saturation in broth with kanamycin. The cultures were then diluted to $^1/_{10000}$ into a broth without kanamycin and grown to saturation. Two further cycles of dilution and growth were carried out, corresponding to a total number of 50 generations of bacterial growth. The cultures were diluted so that 0.1 ml of the bacterial suspension plated out on a non-selective medium gives nearly 300 single colonies per plate. 100 of these colonies were patch plated onto both selective and non-selective media plates. The % of kananycin-resistant colonies corresponds to the fraction of the cell population that maintains the plasmid integrated in the genome. 95% of the *M. smegmatis* cells conserve the plasmid pAV8800 integrated in their genomes after 50 generations in a non-selective medium. By contrast, in BCG pAV8800 is not stable. pAV1, which includes only the attP-int region, can be safely maintained in the *M. smegmatis* and BCG genomes after 50 generations without kanamycin.

TABLE 2

Stability of the integrative plasmids

| Mycobacteria spp. | plasmid | % kanamycin-resistant colonies |
|---|---|---|
| *M. smegmatis* mc2155 | pAV8800 | 95 |
| | pAV1 | 100 |
| | pAV3 | 100 |
| *M. bovis* BCG | pAV8800 | 0 |
| | pAV1 | 97 |

Despite the excellent stability of the pAV1 transformants of BCG, for safety reasons a new integrative vector was constructed, pAV3 (FIG. 11), which only contains the Ms6 attP region, meaning that the integrase gene was excluded. Therefore, the int gene will not be present in the genome of the recombinant mycobacteria produced to guarantee the stability of the genetic construction. The integrase required for recombination is provided by a suicide vector . The stability of the transformants containing the pAV3 inserted in the genome is 100%, in both M.smegmatis and BCG.

EXAMPLE 2

Construction of Integrative Expression Plasmids Derived from the att-int Locus of the Mycobacteriophage Ms6

A. Elimination of a BamHI Site of the int Gene by Directed Mutagenesis

Figure 12:
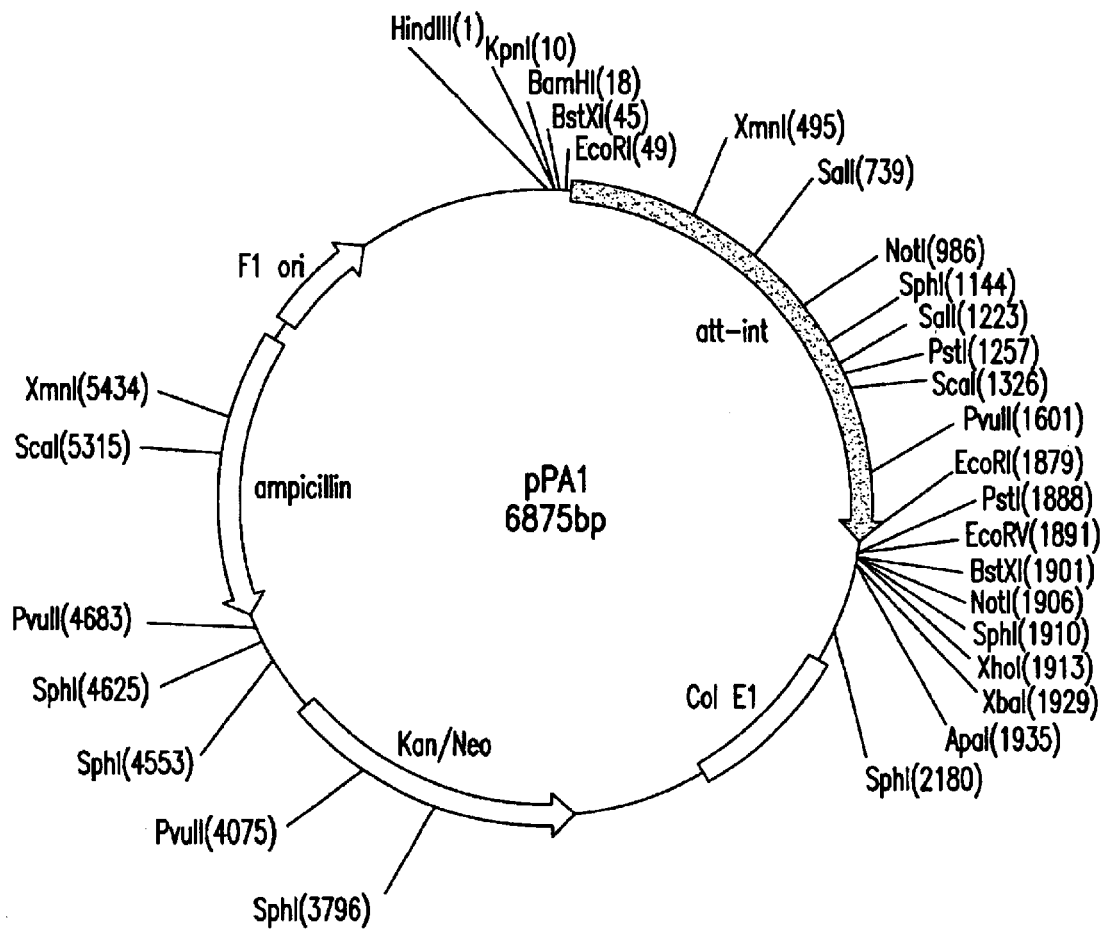
FIG. 12: Map of plasmid pPA1. pPA1 resulted from pAV1 by elimination of the BamHI restriction site present in the int gene. The cytosine at position 931 of the DNA sequence SEQ ID NO: 16 was changed into a thymidine using Stratagene's QuickChange™ Site-Direct mutagenesis kit.

To facilitate future manipulations, the restriction site BamHI in the int gene was eliminated by means of a point mutation. The cytosine in position 769 of an Ile codon was changed into a Tymidine (ATC/ATT). This point mutation does not change the amino acid to be inserted in that position since the ATT codon also encodes an Ile residue. This point mutation was carried out using Stratagene's QuickChange™ Site-Direct mutagenesis kit. The initiating sequences used to perform this point mutation had the following base sequence: pA: 5'GTGGTGCCGAATCCATTC-3' (SEQ ID NO:5) and pT: 5'-GCCGAATGGATTCGGCACCAC-3' (SEQ ID NO:6). The underlined bases are responsible for the point mutation. This technique was utilized to eliminate the BamHI site in position 820, in the int gene, of the plasmid pAV1 resulting in the cloning plasmid pPA1 (FIG. 12), which contain a single BamHI restriction site.

Figure 13:
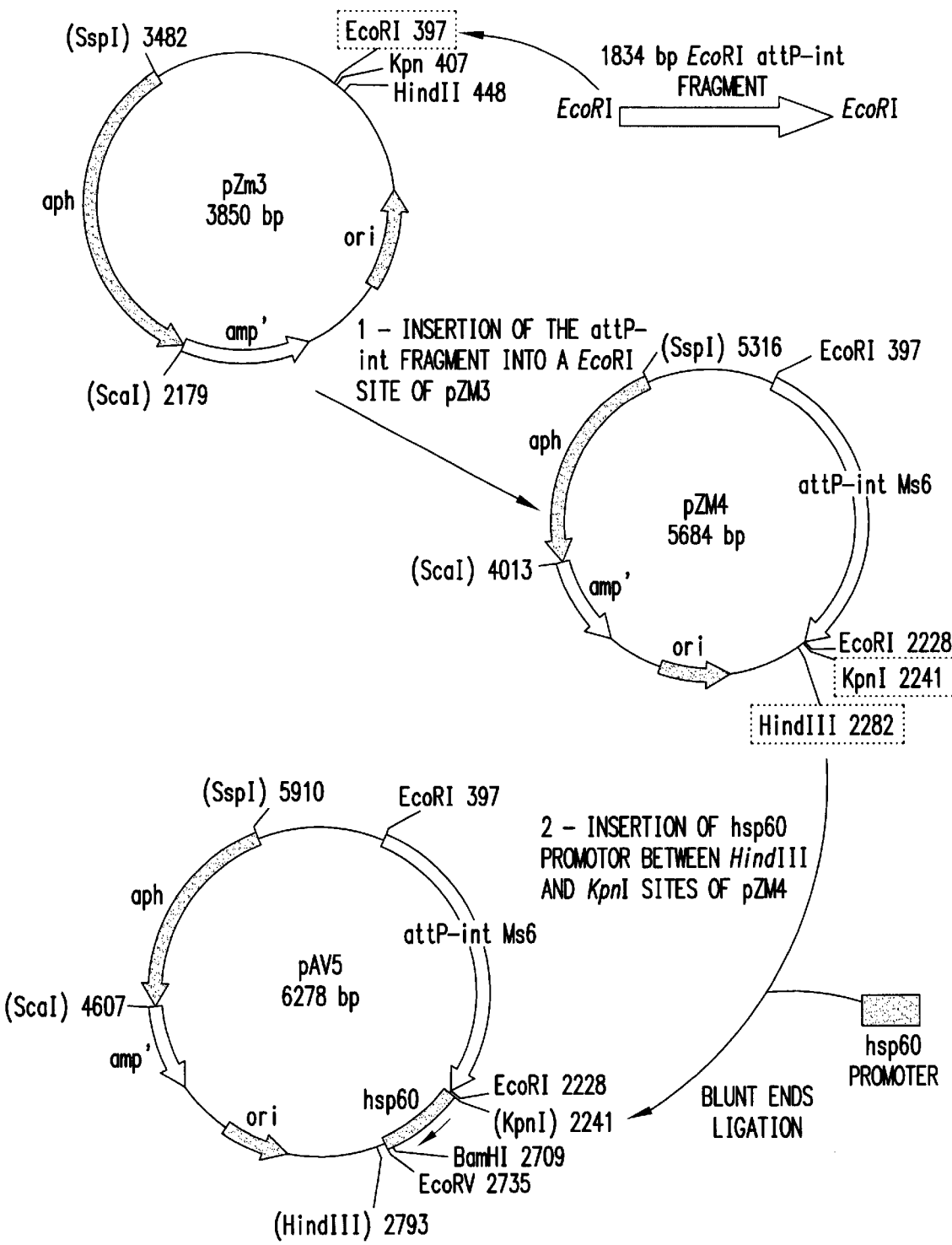
FIG. 13: Strategy followed for the construction of the expression integrative plasmid pAV5. A 1834 bp EcoRI attP-int fragment obtained from plasmid pPA1 was inserted into the single site EcoRI of plasmid pZM3. This plasmid is a derivative of the pUC19 (Yanisch-Perron, C., Vieira, J. and Messing, J. (1985) Gene 33, 103–119) where the aminoglycoside phosphotransferase gene (aph) from Tn5 was inserted between the sites ScaI and SspI. The recombinant plasmid obtained pZM4, was digested with KpnI, filled in with the T4 polymerase and digested with HindIII resulting a blunt/HindIII ends linear plasmid DNA. Mycobacterial expression cassettes including, promoter and translation initiation signals were inserted between restriction sites HindIII and XbaI of pZM4.
Figure 14:
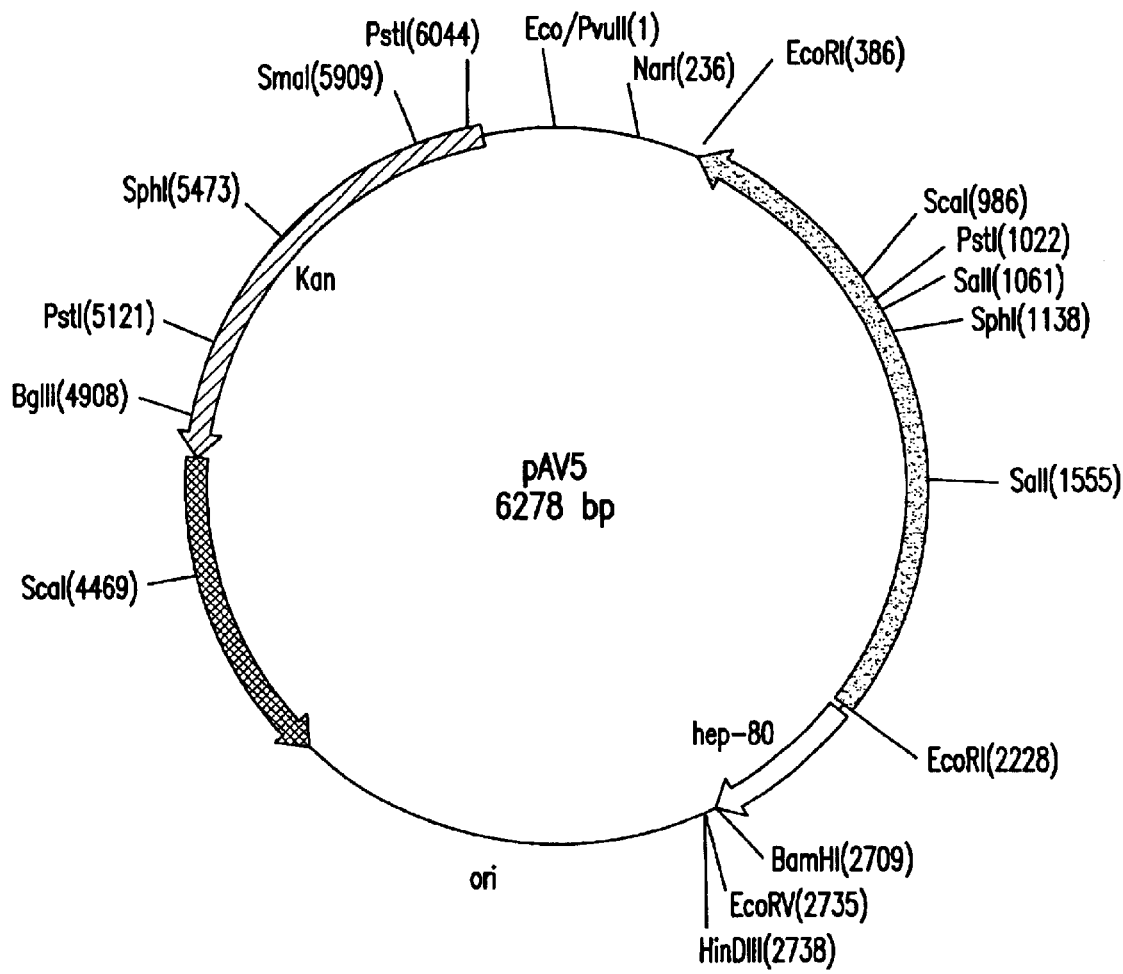
FIG. 14: Map of plasmid pAV5. pAV5 is an expression integrative plasmid containing the attP-int region of mycobacteriophage Ms6, the promoter region, the translation initiation signals and the first 6 codons of the BCG hsp60 gene followed by a multiple cloning site (SEQ ID NO: 49). The genes to be expressed in mycobacteria are fused with the 5' end of hsp60 gene. This expression cassette was removed from plasmid pSMT3, (Peader O'Gaora et al. 1994).
Figure 15:
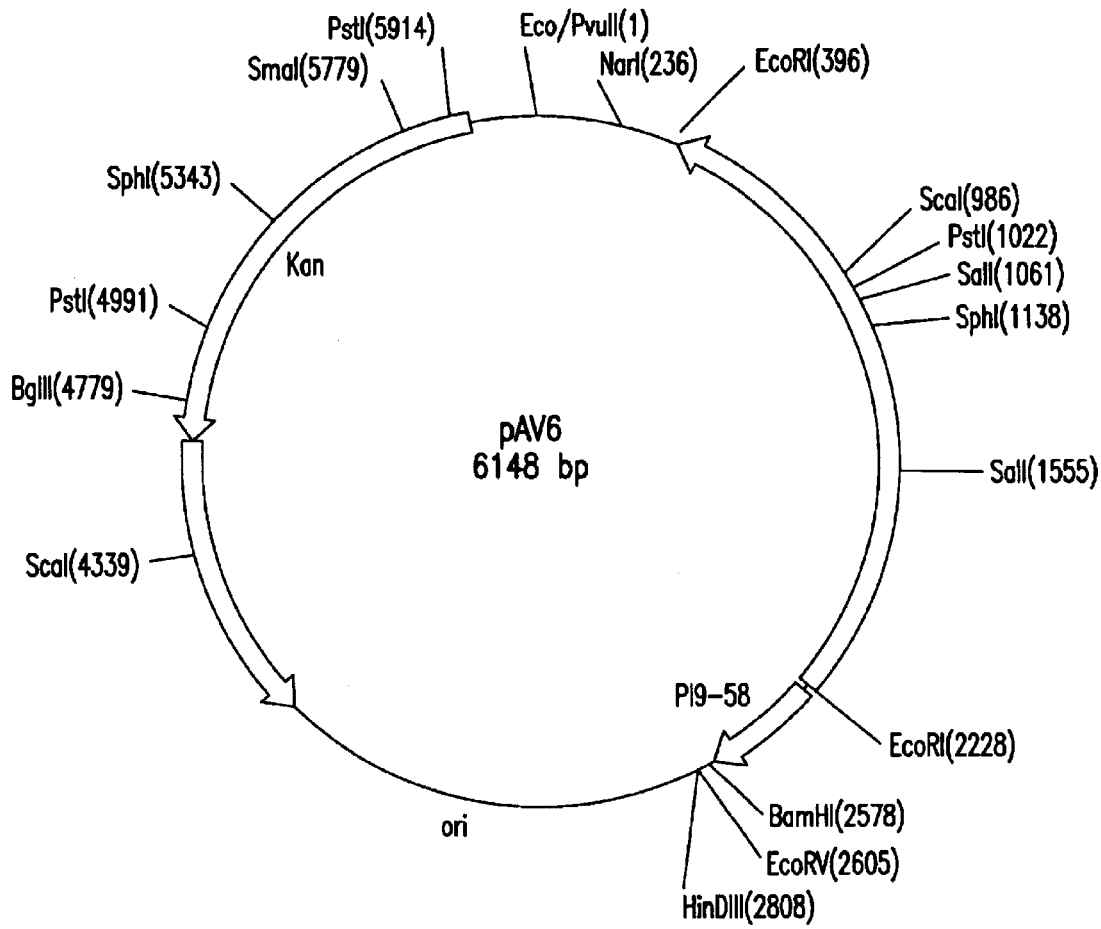
FIG. 15: Map of plasmid pAV6. pAV6 is an expression integrative plasmid containing the attP-int region of mycobacteriophage Ms6, the promoter region, the translation initiation signals and the first codons of the M. tuberculosis 19-kD antigen gene followed by a multiple cloning site (SEQ ID NO: 50). The genes to be expressed in mycobacteria are fused with the 5' end of mtb 19 gene. This expression cassette was removed from plasmid pAU151 (Peader O'Gaora et al. 1994).
Figure 16:
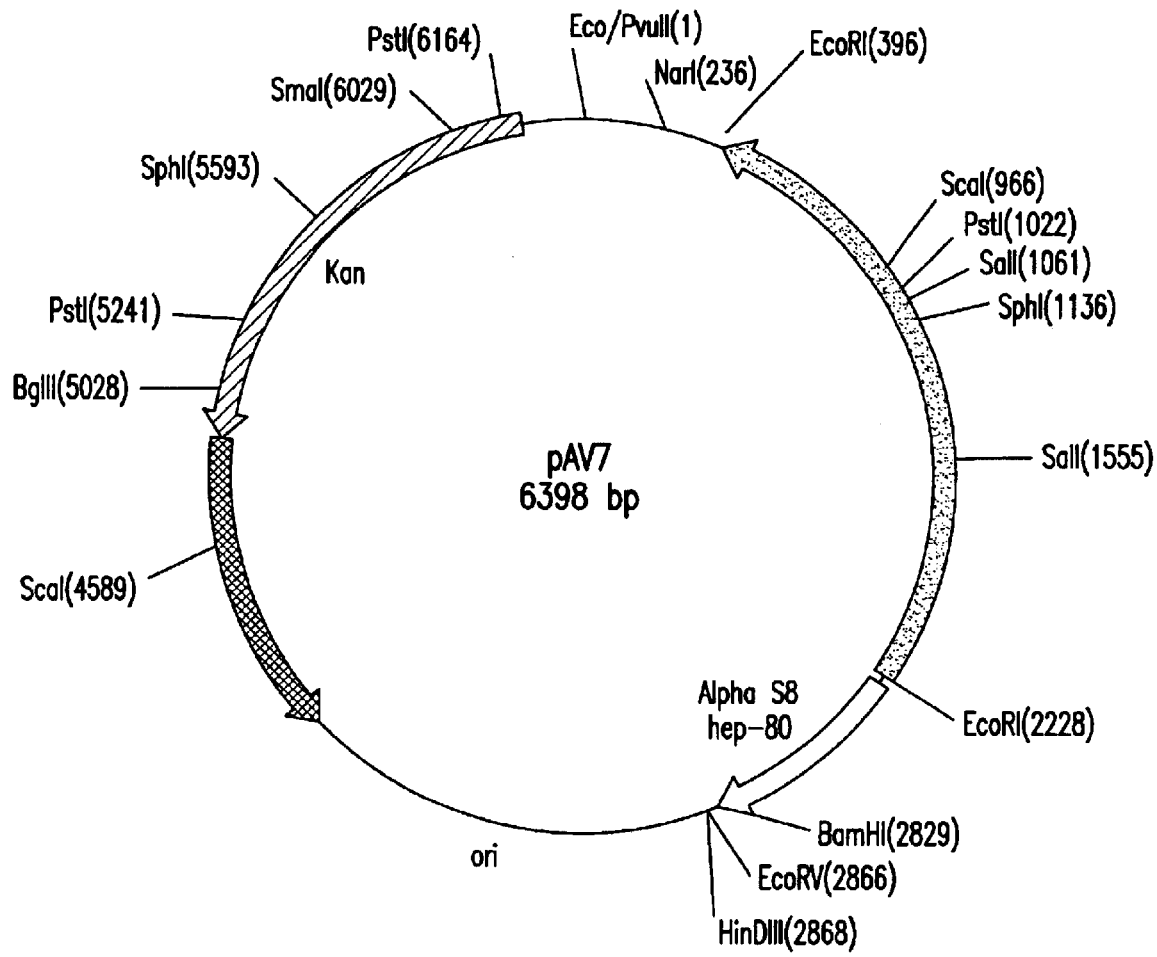
FIG. 16: Map of plasmid pAV7. pAV7 is an expression integrative plasmid containing the attP-int region of mycobacteriophage Ms6, the promoter region, the translation initiation signals and the first codons of the *M. tuberculosis* a antigen gene followed by a multiple cloning site (SEQ ID NO: 51). The genes to be expressed in mycobacteria are fused with the 5' end of mtb α gene. This expression cassette was removed from plasmid pDE22 (Peader O'Gaora et al.1994).

Construction of plasmids including mycobacterial promoter expression cassettes. Plasmid pPA1 was digested by EcoRI in order to separate by gel electrophoresis the EcoRI fragment which contains the attP-int region. This fragment was attached to the plasmid pZM3 previously digested with the same restriction enzyme to create pZM4 (FIG. 13). This plasmid was digested with KpnI and the ends were filled with the T4 polymerase and then digested with HindIII; resulting in DNA with blunt ends. Expression cassettes, including promoter and translation initiation signals, of BCG hsp60, M.tb 19 kDa protein and a hybrid comprising the Hsp60 promoter and the translational signals of the M.tb alfa antigen genes were inserted between restriction sites HindIII and XbaI of pZM4 to produce the plasmids pAV5 (FIG. 14) (SEQ ID NO:49), pAV6 (FIG. 15) (SEQ ID NO:50) and pAV7(FIG. 16) (SEQ ID NO:51. These expression cassetes were removed respectively from plasmids pSMT3, pAU151 and pDE22 constructed by Peadar O'Gaora et al., 1994. First, the plasmids were digested with XbaI and the XbaI ends were flushed with T4 DNA polymerase. Secondly, a HindIII digestion was carried out to produce small DNA fragments blunt HindIII ends containing the expression cassettes. These fragments were attached to the blunt HindIII ends of the linear plasmid ZM4. Relevant DNA sequences can be fused with one of these expression cassettes using the multiple cloning site located at the 3' end.

EXAMPLE 3

DNA Integration by Trans-complementation

A. Construction of the Integrative Plasmid pAV3

The minimal functional attP region of the Ms6 was defined by performing a series of deletions at the 5' end of the att-int fragment used to construct the plasmid pAV1 and checking for the capacity of each deletion to direct the integration into the *M. smegmatis* genome. The deleted fragments were obtained by PCR using the following initiating sequences at the 5' end:

pC2 5'-GATCCGGGCCTCGTACTCG-3' (SEQ ID NO:7)

p13 5'-CAGCAGACACCCACATGTCCG-3' (SEQ ID NO:8)

p1C 5'-CGCTACAGGTCTAAAAAGGTCGG 3' (SEQ ID NO:9)

pC 5'-AGGGGTTCGAATCCCCTTAGCTCCAC-3' (SEQ ID NO:10)

At the 3' end the primer p10, 5'-CAACCCGACGGTGTTGCG-3' (SEQ ID NO:54) was always used. Therefore, with the pair of primers pC2/p10 a fragment of 1818 bp was obtained; with the pair of primers p13/p10 a fragment of 1521 bp; with the pair of primers p1C/p10 a fragment of 1459 bp and with the pair of primers pC/p10 a fragment of 1382 bp. All these PCR products were cloned into the pCR3 plasmid and electroporated into *M. smegmatis* cells. The transformation efficiency, the number of kanamycin-resistant colonies/µg of DNA of each plasmid was determined and the results are shown in the Table 3.

TABLE 3

| DNA fragment (bp) | Transformation efficiency |
|---|---|
| 1818 | $1.10^5$ |
| 1521 | $1.10^5$ |
| 1459 | 0 |
| 1382 | 0 |

The results of the transformation efficiency show that the fragment of 1521 bp is the smallest functional integrative cassette. The fragment 1459 bp with 62 bp less is not functional which means that in this short piece of DNA there are sequences which are important for site-specific recombination.

Figure 11:
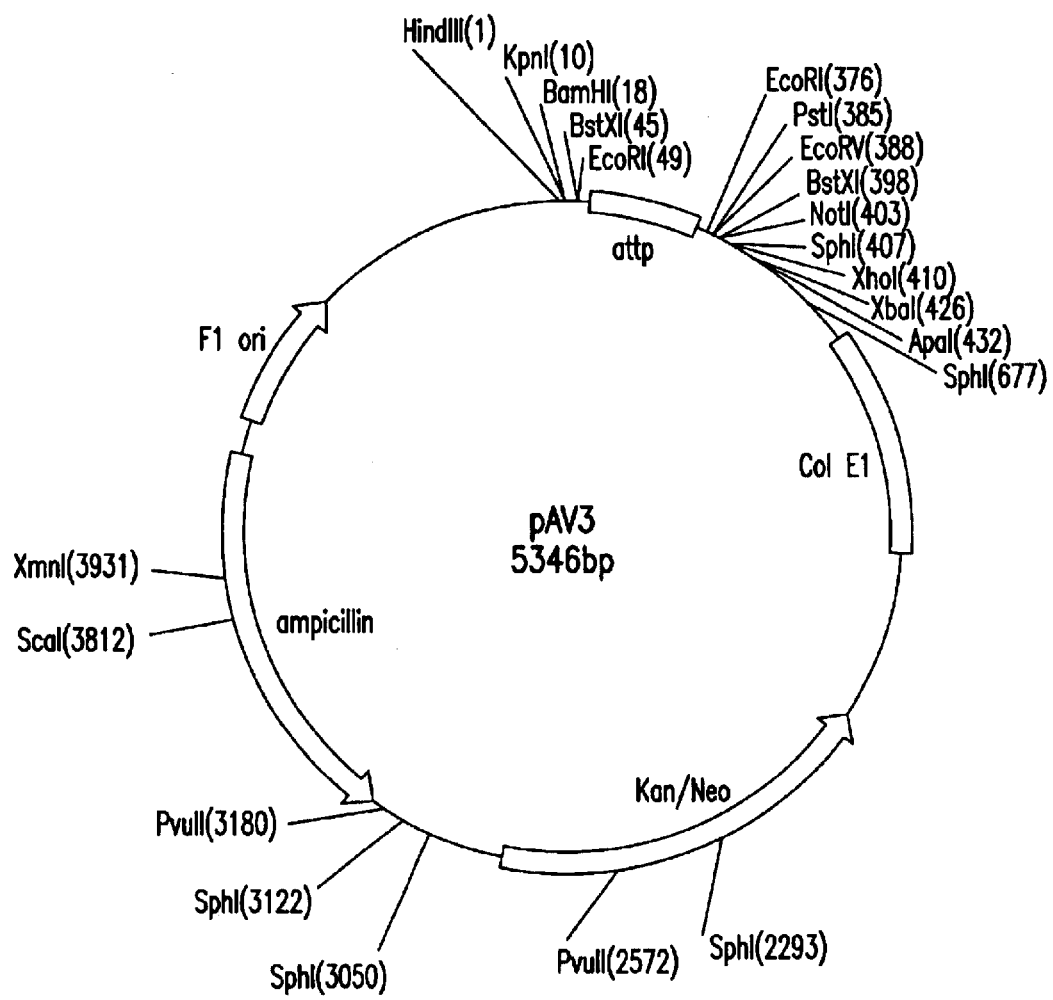
FIG. 11: Map of plasmid pAV3. pAV3 was constructed by inserting Ms6 attP region into the cloning site of the plasmid pCR3 (Invitrogen). The attP region was obtained by direct amplification (PCR) from Ms6 DNA using primers p13 (SEQ ID NO: 8) and p2N (SEQ ID NO: 11).

A recombinant plasmid containing the attP region of the bacteriophage was constructed. The attP region was obtained by direct amplification from the phage DNA, using PCR and the pair of primers p13/p2N (5'-GTTCCGTCTTTGCGGACCC-3' (SEQ ID NO:11)). The amplicon of 273 bp was cloned into the plasmid pCR3 produce the plasmid pAV3 (FIG. 11).

B. Construction of the Suicide Helper Vector pAV4

Figure 18:
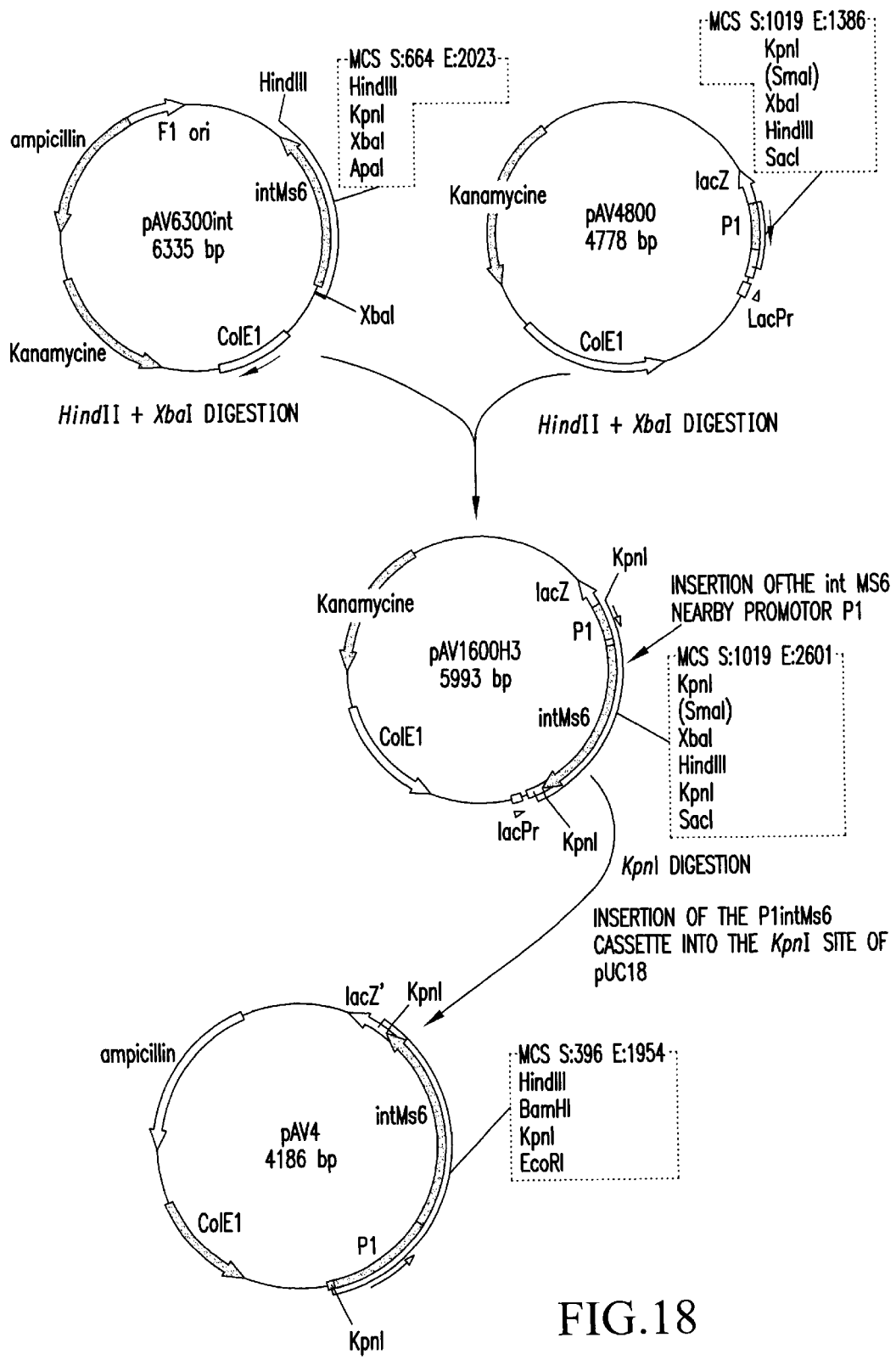
FIG. 18: Strategy followed for the construction of plasmid pAV4. pAV4 resulted from the insertion of the fusion between the Ms6 promoter P1 (SEQ ID NO: 52) and the Ms6 integrase gene in the pUC19 vector (Yanisch-Perron, C., Vieira, J. and Messing, J. (1985) Gene 33, 103–119). The integrase gene was obtained by PCR from Ms6 DNA using primers p1896 (SEQ ID NO: 13) and primer p661 (SEQ ID NO: 12). The produced amplicon was closed in pCR3 (Invitrogen) resulting the plasmid pAV6300int. This plasmid was double digested with HindIII and XbaI enzymes and the fragment int was then inserted in plasmid pAV4800 to generate plasmid pAV1600H3. pAV400 possesses the promoter P1 sequence upstream of the single sites XbaI and HindIII where the int gene was inserted. The fusion between P1 and the int gene present in a KpnI fragment of plasmid pAV160OH3 was transferred to pUC19 to generate plasmid pAV4.

Insertion of a strong promoter region upstream of the int gene. A strong promoter region (P1) from the mycobacteriophage Ms6 was identified by inserting Sua3AI restriction fragments into the multiple cloning site of the promoter probe plasmid pJEM15 described in J.Timm et al., J.Bacteriol. Vol. 176. p.6749–53 (1994). The DNA sequence of this promoter region was determined and is represented in FIG. 17 (SEQ ID NO:52). A suicide plasmid vector containing the int gene under the control of the P1 promoter was constructed as follows:

The plasmid pMGI which contains the LacZ gene of *E.coli* under the control of the P1 promoter was digested with the KpnI and ScaI restriction enzymes in order to separate the P1 promoter region. The DNA fragment containing P1 was attached to the plasmid CMV (Stratagene), double digested KpnI and SmaI to form the plasmid pAV4800 (FIG. 18). The integrase gene was obtained by PCR from the phage DNA using primers p661 (5'-

CAGCACCGA<u>TCTAGACA</u>CAACGGAT-3' (SEQ ID NO:12)), which generates a restriction site in the the product PCR (amplicon) and p1896 (5'-TCCGCAC <u>AAGCTT</u>CTGCGGAACCTGG-3' (SEQ ID NO:13)), which generates a HindIII restriction site in the other end of the amplicon. This amplicon was inserted into the plasmid pCR3 (Invitrogen), resulting in two different plasmids with respect to the orientation of the amplicon in the multiple cloning site (mcs). The plasmid in which the HindIII site of the amplicon is side by side with the HindIII site of the mcs was chosen, pAV 6300int (FIG. 18).

The HindIII XbaI fragment which encodes the integrase of the pAV6300 was inserted between the HindIII and XbaI restriction sites of the plasmid pAV4800 to form plasmid pAV1600H3. Finally, the KpnI fragment, carrying the P1-int gene, was cloned into the KpnI site of the E.coli plasmid pUC18 to generate the plasmid pAV4 (FIG. 18).

C. Experiment of Trans-integration

To improve the stability of the recombinant mycobacteria a site-specifc integration process was developed using the int gene in a suicide vector and the attP region in another plasmid in association with the foreign gene(s) to be expressed. With this process the integrated DNA fragment does not codify either the integrase or the excisionase functions, which are both required for the excision process. Therefore, the probability of excision is reduced to a very low level which allow us to expect that the foreign DNA will be maintained forever.

A first recombinant plasmid, referred to as the helper vector (pAV4), which does not contain any bacterial origin of replication (suicide vector) was used to transiently produce the int protein required for mediating the integration process. The helper vector includes 1) the int gene under the control of a strong P1 mycobacterial promoter; 2) the E. coli plasmid vector pUC18.

A second recombinant vector, referred to as the integrating vector (pAV3), which was used to introduce the relevant DNA into a specific site of the mycobacterial genome. The integrating vector includes: 1) the attP region of the Ms6 mycobacteriophage; 2) DNA that encodes a selective marker of mycobacterial origin; 3) DNA that encodes a strong and regulated mycobacterial promoter region to control or direct the expression of the relevant DNA; 4) the relevant DNA that encodes vaccinal antigens, immunomodulators and polypeptides or proteins of interest.

To produce a stable recombinant mycobacteria, the helper and the integrating plasmids were mixed and electroporated into mycobacterial cells (this system applies to both fast and slow-growing mycobacteria including BCG). The transformed cells were plated onto a medium containing kanamycin. The kanamycin-resistant transformants can be isolated with a transformation efficiency of about $4.10^4$ colonies/μg of DNA. The presence of the integrative plasmid within the bacterial genome was confirmed using a Southern/hybridization using the attP region as a probe. The stability of the recombinant mycobacteria produced was 100% (all the transformants conserved their kanamycin-resistance after 50 generations in a non-selective medium).

This experiment demonstrated, for the first time, that it is possible, using the site-specific integration system of mycobacteriophage Ms6, to integrate DNA into the mycobacteria genome using a trans-complementation process.

EXAMPLE 4

Construction of an Integrative Expression Vector Based on the Ms6 P1 Promoter

The P1 promoter region of the bacteriophage Ms6 strongly expresses the LacZ reporter gene at high levels in both fast and slow-growing Mycobacterium spp, including BCG. This transcriptional fusion, carried out by the plasmid pMG1, includes the P1 promoter and CII-LacZ hybrid gene (fusion between the translation initiation signals of the CII gene of the bacteriophage λ with the E.coli LacZ gene at its 5' truncated end). FIG. 19 shows the DNA sequence of this construction.

A DNA fragment (cassette) encoding the P1-CII-LacZ expression control sequences (i.e. promoter and translation signals) was produced by PCR using the primers pm4 (5' end) and pm2 (3' end) and, as the DNA target, the plasmid pMG1. The primers have the following base sequences:

pm4:
  5'-CCCTTAATAGATTATATTACTAATTATTGGGG-3' (SEQ ID NO:14)

pm2: 5'-TCCGATTCGTAGAGCCTCG-3' (SEQ ID NO:15)

Figure 20:
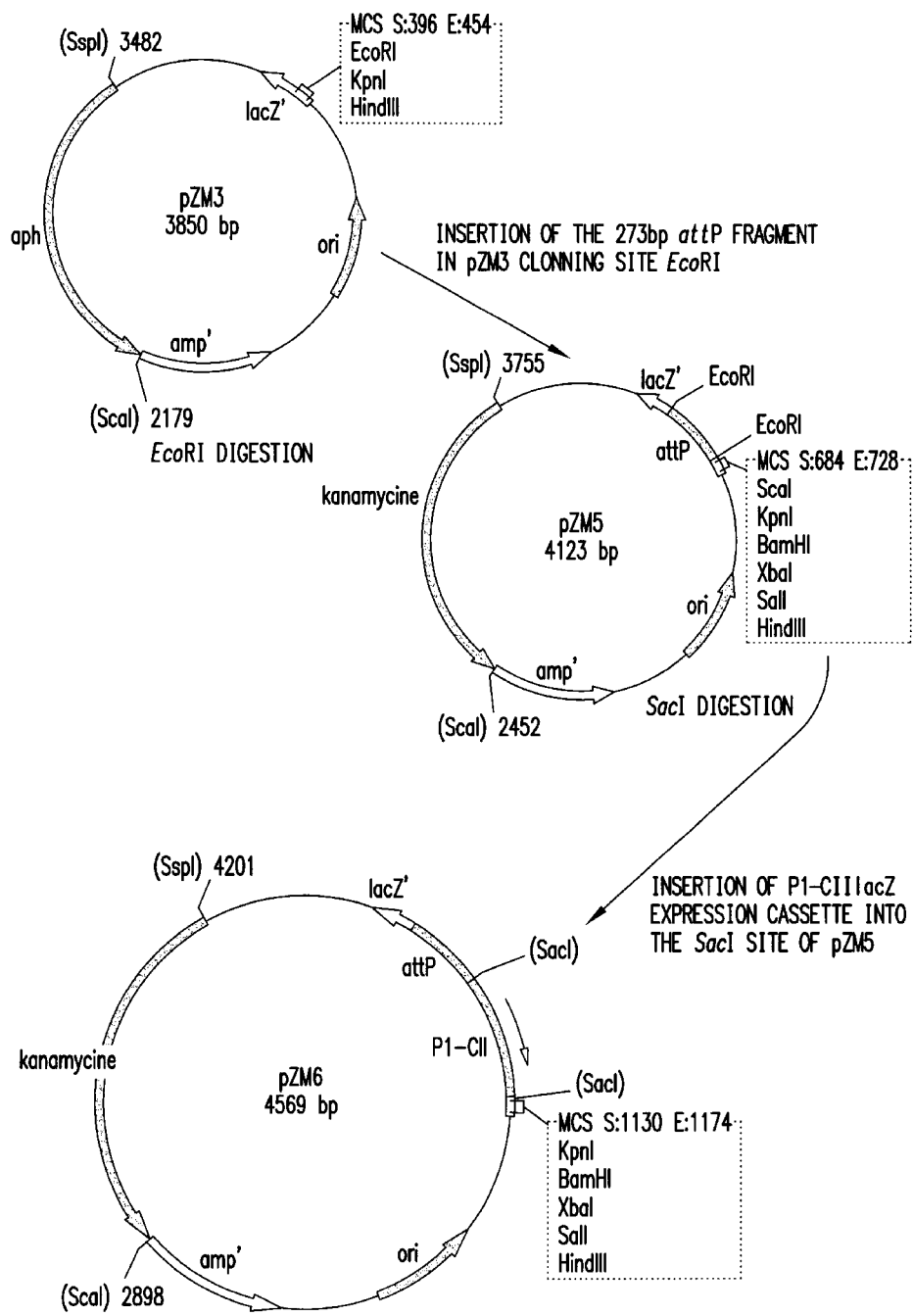
FIG. 20: Strategy followed for the construction of the expression vector pZM6. pAV3 (FIG. 11) was digested with EcoRI to separate the Ms6 attP region. This fragment was cloned in the single site EcoRI of pZM3, generating plasmid pZM5. The expression cassette P1-CII-LacZ (SEQ ID NO: 14) was inserted in the site SacI of the multiple cloning region of plasmid pZM5 resulting plasmid pZM6. pZM6 is a pUC19 derivative plasmid that contains the attP region of mycobacteriophage Ms6 and the expression cassette P1-CII-LacZ.
Figure 21:
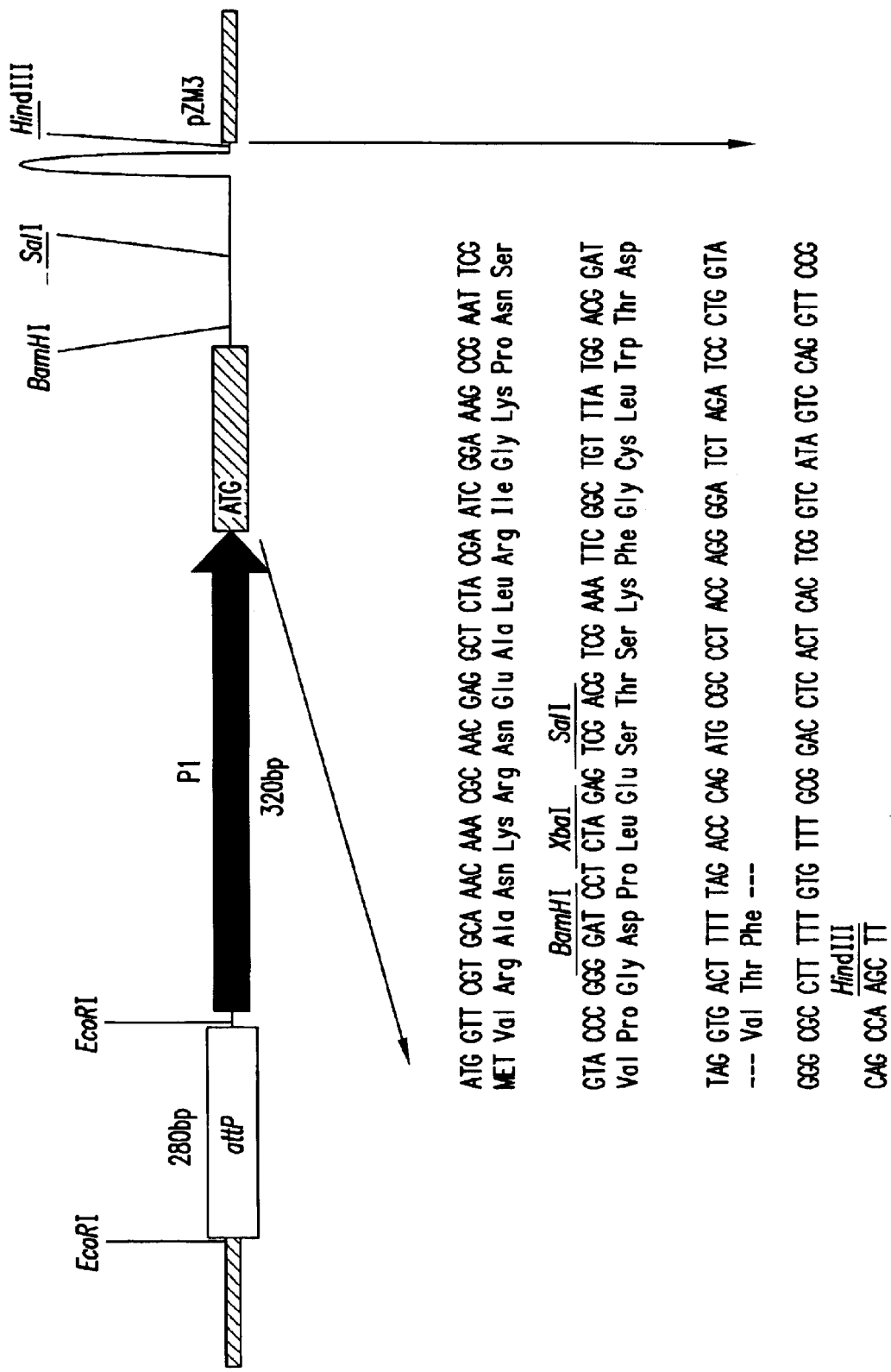
FIG. 21 PZM6 expression vector. The expression cassette comprises the fusion between P1 promoter region. (SEQ ID NO:52) with the translation signals and the 5' end sequence of 1 CII gene, followed by a multiple cloning site and the transcriptional terminator sequence located downstream of mycobacteriophage Ms6 int gene. The DNA sequence from the 5' end of 1 CII gene till the HihdIII restriction site is disclosed.

The amplicon was cloned into the plasmid pCR™3 (Invitrogen) and the resulting plasmid was digested with EcoRI. The short EcoRI fragment of 446 bp was purified by gel electrophoresis and its extremities were filled with the T4 polymerase. This blunt-ended DNA fragment that encodes expression cassette was inserted into the SacI site, previousely flushed with T4 polymerase, of plasmid the pZM5 (FIG. 20). The plasmid pZM5 was obtained from the insertion of the pAV3 EcoRI restriction fragment, which contains the attP sequence of the phage Ms6, into the EcoRI site of the plasmid ZM3 (FIG. 20). The resulting integrative expression plasmid was named pZM6 (FIG. 20). FIG. 21 represents the DNA sequence of the pZM6 expression cassette and the multiple cloning site. Gene fusions with the 5' end of the CII-LacZ gene can be obtained by inserting the DNA to be expressed into the multiple cloning site of the plasmid Zm6. These fusions will be under the control of the P1 promoter region. The plasmid pZM6 can mediate the integration, by trans-complementation and the expression of gene fusions in Mycobacterium.

The integrative expression plasmid vector described in the trans-complementation technique can also carry other mycobacterial promoter regions such as: BCG HSP60, the 19 kDa antigen of M.tuberculosis or of the M. fortuitum bla gene.

EXAMPLE 5

Cloning of Antigen Genes in Expression Cassettes

A series of antigen genes can be expressed by BCG using the methodology developed in this application. Expression cassettes were constructed by PCR and cloned into the multiple cloning site of pZM5 (FIG. 20). The following antigen genes can be fused with pZM6-derived expression cassettes:

HIV-1: env; gag; transmembrane gp 41 gene; vif.

HIV-2: env; gp36; gag; vif.

FIV: env glicoproteins; gag polyprotein; vif

Hepatitis B Virus: pre-S1; pre-S2 and S antigens

Leishmania: Surface glycoproteins GP 63 and GP43; proteins LNP18 and P32.

It is to be understood, however, that the scope of the present invention described above is not to be limited to the specific embodiments described. The invention may be put into practice other than as specifically described and still fall within the scope of the accompanying claims.

What is claimed is:

1. A genetic system for integrating DNA into a specific site of a *Mycobacterium* spp. genome comprising:
   a) a first DNA consisting of the nucleotide sequence shown in SEQ ID NO:16 linked to a heterologous DNA of interest, wherein said heterologous DNA of interest encodes peptides, polypeptides or proteins that are expressed under the control of a promoter region; or,
   b) a combination of two plasmids, wherein the first plasmid comprises the phage attachment site (attp) having the sequence shown in nucleotides 462 to 729 of the nucleotide sequence shown in SEQ ID NO:16, and the heterologous DNA of interest under the control of a promoter region, and wherein the second plasmid comprises a DNA sequence of a phage integrase shown in nucleotides 697 to 1921 of the nucleotide sequence shown in SEQ ID NO:16.

2. An integrative plasmid for cloning DNA in Mycobacterium spp. comprising:
   a) the first DNA sequence of claim 1a), wherein said heterologous DNA of interest is under the control of a mycobacterial promoter region;
   b) an *E. coli* origin of replication; and
   c) a selective marker for mycobacteria.

3. The genetic system of claim 1, wherein said first plasmid further comprises
   a) a mycobacterial promoter region that controls expression of said heterologous DNA of interest;
   b) an *E. coli* origin of replication; and
   c) a DNA encoding a selective marker for mycobacteria.

4. A recombinant mycobacteria comprising a foreign, heterologous DNA of interest under the control of a myco-bacterial promoter region, wherein said heterologous DNA of interest is inserted into the genome using the genetic system of claim 1.

5. The genetic system of claim 1, wherein said Mycobacterium spp. is a strain selected from the group consisting of *Mycobacterium tuberculosis, M. bovis*-BCG, *M. smegmatis, M. vaccae, M. avium, M. intracellulare, M. fortuitum,* and *M. genovences*.

6. A purified and isolated DNA sequence of the integration locus from mycobacteriophage Ms6 DNA consisting of the nucleotide sequence shown in SEQ ID NO:16.

7. The isolated and purified DNA of claim 6, wherein said integration locus comprises the bacteriophage attachment site (attP) and the integrase gene.

8. A genetic system for integrating DNA into a specific site of a Mycobacterium spp. genome comprising:
   a) a first DNA consisting of the nucleotide sequence shown in SEQ ID NO:16 linked to a heterologous DNA of interest, wherein said heterologous DNA of interest encodes peptides, polypeptides or proteins that are expressed under the control of a promoter region; or,
   b) a combination of two plasmids, wherein the first plasmid comprises the phage attachment site (attP) having the sequence shown in nucleotides 462 to 729 of the nucleotide sequence shown in SEQ ID NO:16, and the heterologous DNA of interest under the control of a promoter region, and wherein the second plasmid comprises
      (a) a DNA sequence of a phage integrase shown in nucleotides 697 to 1921 of the nucleotide sequence shown in SEQ ID NO:16,
      (b) the integrase gene under the control of a mycobacterial promoter;

(c) an *E. coli* origin of replication; and (d) a selective marker for *E.coli*.

9. A purified and isolated DNA from mycobacteriophage Ms6 that promotes the transcription of DNA in Mycobacterium spp. consisting of the nucleotide sequence shown in SEQ ID NO:52.

10. An isolated DNA sequence that hybridizes under stringent conditions with a sequence consisting of SEQ ID NO: 16.

11. An isolated amino acid sequence shown in SEQ ID NO:17.

12. A genetic system for integrating DNA into a specific site of a Mycobacterium spp. genome consisting of:

a) a first DNA consisting of the nucleotide sequence shown in SEQ ID NO:16 linked to a heterologous DNA of interest, wherein said heterologous DNA of interest encodes peptides, polypeptides or proteins that are expressed under the control of a promoter region; or, b) a combination of two plasmids, wherein the first plasmid consists of the phage attachment site (attP) having the sequence shown in nucleotides 462 to 729 of the nucleotide sequence shown in SEQ ID NO:16, and the heterologous DNA of interest under the control of a promoter region, and wherein the second plasmid consists of a DNA sequence of a phage integrase shown in nucleotides 697 to 1921 of the nucleotide sequence shown in SEQ ID NO:16.

\* \* \* \* \*

SEQUENCE LISTING

<160> NUMBER OF SEQ ID NOS: 54

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide P1

<400> SEQUENCE: 1
cgctgttggt gggcctgatc g                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide M1

<400> SEQUENCE: 2
acacgccgga tgaatgacc                                                 19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide C2

<400> SEQUENCE: 3
gatccgggcc tcgtactcg                                                 19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide PRPAV10

<400> SEQUENCE: 4
caacccgacg gtgttgcg                                                  18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide pA

<400> SEQUENCE: 5
gtggtgccga atccattc                                                  18

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide pT

<400> SEQUENCE: 6

```
gccgaatgga ttcggcacca c                                        21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide pC2

<400> SEQUENCE: 7
gatccgggcc tcgtactcg                                           19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide p13

<400> SEQUENCE: 8
cagcagacac ccacatgtcc g                                        21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide p1C
<223> OTHER INFORMATION: Description of Combined DNA/RNA Molecule: tRNA
      ALA

<400> SEQUENCE: 9
cgctacaggt ctaaaaggt cgg                                       23

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide pC

<400> SEQUENCE: 10
aggggttcga atccccttag ctccac                                   26

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide p2N

<400> SEQUENCE: 11
gttccgtctt tgcggaccc                                           19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide p661
```

-continued

```
<400> SEQUENCE: 12
cagcaccgat ctagacacaa cggat                                            25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide p1896

<400> SEQUENCE: 13
tccgcacaag cttctgcgga acctgg                                           26

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide pm4

<400> SEQUENCE: 14
cctttaatag attatattac taattattgg gg                                    32

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide pm2

<400> SEQUENCE: 15
tccgattcgt agagcctcg                                                   19

<210> SEQ ID NO 16
<211> LENGTH: 2404
<212> TYPE: DNA
<213> ORGANISM: Mycobacterium phage Ms6
<220> FEATURE:
<221> NAME/KEY: CDS
<222> LOCATION: (697)..(1812)

<400> SEQUENCE: 16
tccggcgcgg ggggtcatcg cacgtcctcc tcgtaccagg ccaaggcgac gggatcgcca      60
tcgtcggccc tgcggctgat ctcatcgacc aggtcgttga tcttccgctg ccggagaca     120 gcgcgggtcg agcccagctg gcacttcacc cagcgacctg cgatccgggc ctcgtactcg    180
gcgatcagat ccgaggtggt gatggtgctc attttggagt tcctttctgt gtgcctgata   240
cgtccagaat acagcaccct cgttacgagt caaggggttc ggccccacca atttctcgtt   300
acgtcgaaag tccgcgtttc cgcacacggg ggtgccgcat atacaggggc gctgtgcaca   360
ggggtgtggg cagcagcagg gggctagggc acaggggtag gtgagggtgt gggccgcgag   420
ggcctcagcc ccccgctcac gcgcaaccgc cgctcggtat tcagcagaca cccacatgtc   480
cgtgttgtca ctgacaacac ggctccaggt tttcccaggt cgctacaggt ctaaaaaggt   540
cggaacagaa ccacacgggt gttttttcgc aggtaaacgc ccatttcccc acgatcgaag   600
gggttcgaat cccccttagct ccacccaaaa ccgcaggtca gcgaatcgcc cagaatctga   660
cagcaccgat gacatcacaa cggatagaat ccgggt atg gca tca gtg cgt gaa     714
                                        Met Ala Ser Val Arg Glu
                                          1               5
```

|  |  |
|---|---|
| cgg gtc cgc aaa gac gga acc acc gcc tac ctg gtc tcc tac cgg ttc<br>Arg Val Arg Lys Asp Gly Thr Thr Ala Tyr Leu Val Ser Tyr Arg Phe<br>            10              15             20 | 762 |
| ggc gga aga gga agc gca caa ggc gca ctc acc ttc gac aat cgc aaa<br>Gly Gly Arg Gly Ser Ala Gln Gly Ala Leu Thr Phe Asp Asn Arg Lys<br>   25              30              35 | 810 |
| gca gca gac gcc ttc gcc gcc gcc gtc gac gcc cac ggt gct gca cgc<br>Ala Ala Asp Ala Phe Ala Ala Ala Val Asp Ala His Gly Ala Ala Arg<br>40              45              50 | 858 |
| gcc ctg gag atg cac ggc atc aac ccc gca ccg cga gga acc aag tcc<br>Ala Leu Glu Met His Gly Ile Asn Pro Ala Pro Arg Gly Thr Lys Ser<br>55             60             65                  70 | 906 |
| gag ctg acc gtc gcc gaa tgg atc cgg cac cac atc gac cac ctc acc<br>Glu Leu Thr Val Ala Glu Trp Ile Arg His His Ile Asp His Leu Thr<br>            75              80              85 | 954 |
| ggc gtc gag cag tac acg atc gac aaa tac gag cag tac ctc gcc aac<br>Gly Val Glu Gln Tyr Thr Ile Asp Lys Tyr Glu Gln Tyr Leu Ala Asn<br>                90              95            100 | 1002 |
| gac atc gaa ccc aac ctc ggc gac atc ccc ttg tcg aag ctc tcc gaa<br>Asp Ile Glu Pro Asn Leu Gly Asp Ile Pro Leu Ser Lys Leu Ser Glu<br>         105            110            115 | 1050 |
| gag gac atc gcc cgc tgg gtg aag gtc atg gaa acc acc ggc ggc cgc<br>Glu Asp Ile Ala Arg Trp Val Lys Val Met Glu Thr Thr Gly Gly Arg<br>120               125             130 | 1098 |
| gac ggc aac ggg cac gcc ccg aaa acc ctc cgc aac aaa tac ggg ttc<br>Asp Gly Asn Gly His Ala Pro Lys Thr Leu Arg Asn Lys Tyr Gly Phe<br>135             140            145           150 | 1146 |
| cta tcg ggg gca ctg aac gcc gcc gtc ccc cga tac ttg tcc acc aac<br>Leu Ser Gly Ala Leu Asn Ala Ala Val Pro Arg Tyr Leu Ser Thr Asn<br>               155            160           165 | 1194 |
| cct gcg tcg ggc cgc cgc ctg ccc cgt ggg aac gct gag gac gac gac<br>Pro Ala Ser Gly Arg Arg Leu Pro Arg Gly Asn Ala Glu Asp Asp Asp<br>         170            175            180 | 1242 |
| gag atc cgc atg ctc acc cac gcc gag ttc gac cgg ctc cgc gac gcg<br>Glu Ile Arg Met Leu Thr His Ala Glu Phe Asp Arg Leu Arg Asp Ala<br>185             190             195 | 1290 |
| gtg aca cct cac tgg aag ctg atg gtt cag ttc atg gtg tcg acc ggt<br>Val Thr Pro His Trp Lys Leu Met Val Gln Phe Met Val Ser Thr Gly<br>200             205             210 | 1338 |
| ttg cgg tgg ggt gag gta tcg gcg ctg cag ccc agg cat gtg gat ttg<br>Leu Arg Trp Gly Glu Val Ser Ala Leu Gln Pro Arg His Val Asp Leu<br>215             220            225           230 | 1386 |
| gag acg tcc acg atc agg gtg cgg cag gcg tgg aag tac tcg tcg gcc<br>Glu Thr Ser Thr Ile Arg Val Arg Gln Ala Trp Lys Tyr Ser Ser Ala<br>               235            240           245 | 1434 |
| ggg tat gtg ttg ggg ccg ccg aag acg aaa cgg tcc cgc cgc acg gtg<br>Gly Tyr Val Leu Gly Pro Pro Lys Thr Lys Arg Ser Arg Arg Thr Val<br>         250            255            260 | 1482 |
| gat gtg ccg gcc agg ttg ttg gag cgg ctg gac ttg tcg aac gag ttt<br>Asp Val Pro Ala Arg Leu Leu Glu Arg Leu Asp Leu Ser Asn Glu Phe<br>265             270            275 | 1530 |
| gtt ttc gtc aat acc gat ggt gga ccg gtc agg tat ccg ggg ttt ctg<br>Val Phe Val Asn Thr Asp Gly Gly Pro Val Arg Tyr Pro Gly Phe Leu<br>280             285            290 | 1578 |
| cgt agg gtg tgg aat ccg gct gtg gag aag gct ggt ctg gtt ccg cgg<br>Arg Arg Val Trp Asn Pro Ala Val Glu Lys Ala Gly Leu Val Pro Arg<br>295             300            305           310 | 1626 |
| cct act ccg cac gat ctg cgg cac acg tac gcg tcg tgg cag cta acg<br>Pro Thr Pro His Asp Leu Arg His Thr Tyr Ala Ser Trp Gln Leu Thr | 1674 |

```
                315                 320                 325
ggc ggg aca ccg gtg acg att gtg tct cgc cag ctg ggt cat gag tcg      1722
Gly Gly Thr Pro Val Thr Ile Val Ser Arg Gln Leu Gly His Glu Ser
            330                 335                 340 att cag atc acg gtg gac acg tac acg gat gtg gat cgg acg agt tcg      1770
Ile Gln Ile Thr Val Asp Thr Tyr Thr Asp Val Asp Arg Thr Ser Ser
        345                 350                 355 cgg gtg gcg gcg gag ttt atg gac gga ttg ttg ggg gac ttt              1812
Arg Val Ala Ala Glu Phe Met Asp Gly Leu Leu Gly Asp Phe
    360                 365                 370 taagacccag atgcgcccta ccaggggatc tagatccctg gtagggcgcc ttttgtgtt     1872 tgcggacctc actcggtcat agtccaggtt ccgcagccgc ttgtgcggaa catgatgcgg    1932
tggtcgccgt tgatggtgcc ggtccacgac gcaacaccgt cgggttggat gttcgcgcgg    1992
acggtgccgg atgatgcttc accttcgcgg agtgtttcgc cgccgcgata ctcggagacg    2052
ctgacgatgg cccaggtgca gccggggag tcgggtggga tggtgcggt gtaggtgccc      2112 cagtcgtatc cgtctgcgcc gcccatgttg tggtagccgt cgccggggat ggtccgatac    2172
gggttcacgc gcgctgtggt ggtggttgac gttgtggcgg cttgcgttgt ggcgtcgtcg    2232
tccttgtcgc cacgggcgga gacgagggcg acaaggacga ggacgccgag cgcggcggcc    2292
atcacttttc ccagcgagac tgcggcgttg gtgttgttgt tcatggatgt gtgcgctttc    2352
tggtgagggg ctggcaaacg tgacgcactg tcggttatct aatcgtaata tt            2404
```

<210> SEQ ID NO 17
<211> LENGTH: 372
<212> TYPE: PRT
<213> ORGANISM: Mycobacterium phage Ms6

<400> SEQUENCE: 17

```
Met Ala Ser Val Arg Glu Arg Val Arg Lys Asp Gly Thr Thr Ala Tyr
 1               5                  10                  15

Leu Val Ser Tyr Arg Phe Gly Gly Arg Gly Ser Ala Gln Gly Ala Leu
            20                  25                  30

Thr Phe Asp Asn Arg Lys Ala Ala Asp Ala Phe Ala Ala Ala Val Asp
        35                  40                  45

Ala His Gly Ala Ala Arg Ala Leu Glu Met His Gly Ile Asn Pro Ala
    50                  55                  60

Pro Arg Gly Thr Lys Ser Glu Leu Thr Val Ala Glu Trp Ile Arg His
65                  70                  75                  80

His Ile Asp His Leu Thr Gly Val Glu Gln Tyr Thr Ile Asp Lys Tyr
                85                  90                  95

Glu Gln Tyr Leu Ala Asn Asp Ile Glu Pro Asn Leu Gly Asp Ile Pro
            100                 105                 110

Leu Ser Lys Leu Ser Glu Glu Asp Ile Ala Arg Trp Val Lys Val Met
        115                 120                 125

Glu Thr Thr Gly Gly Arg Asp Gly Asn Gly His Ala Pro Lys Thr Leu
    130                 135                 140

Arg Asn Lys Tyr Gly Phe Leu Ser Gly Ala Leu Asn Ala Ala Val Pro
145                 150                 155                 160

Arg Tyr Leu Ser Thr Asn Pro Ala Ser Gly Arg Arg Leu Pro Arg Gly
                165                 170                 175

Asn Ala Glu Asp Asp Glu Ile Arg Met Leu Thr His Ala Glu Phe
            180                 185                 190

Asp Arg Leu Arg Asp Ala Val Thr Pro His Trp Lys Leu Met Val Gln
```

-continued

```
                  195                 200                 205
        Phe Met Val Ser Thr Gly Leu Arg Trp Gly Glu Val Ser Ala Leu Gln
            210                 215                 220

Pro Arg His Val Asp Leu Glu Thr Ser Thr Ile Arg Val Arg Gln Ala
        225                 230                 235                 240

Trp Lys Tyr Ser Ser Ala Gly Tyr Val Leu Gly Pro Pro Lys Thr Lys
                            245                 250                 255

Arg Ser Arg Arg Thr Val Asp Val Pro Ala Arg Leu Leu Glu Arg Leu
                        260                 265                 270

Asp Leu Ser Asn Glu Phe Val Phe Val Asn Thr Asp Gly Gly Pro Val
                    275                 280                 285

Arg Tyr Pro Gly Phe Leu Arg Arg Val Trp Asn Pro Ala Val Glu Lys
                290                 295                 300

Ala Gly Leu Val Pro Arg Pro Thr Pro His Asp Leu Arg His Thr Tyr
        305                 310                 315                 320

Ala Ser Trp Gln Leu Thr Gly Gly Thr Pro Val Thr Ile Val Ser Arg
                            325                 330                 335

Gln Leu Gly His Glu Ser Ile Gln Ile Thr Val Asp Thr Tyr Thr Asp
                        340                 345                 350

Val Asp Arg Thr Ser Ser Arg Val Ala Ala Glu Phe Met Asp Gly Leu
                    355                 360                 365

Leu Gly Asp Phe
            370

<210> SEQ ID NO 18
<211> LENGTH: 28
<212> TYPE: PRT
<213> ORGANISM: Bacteriophage HP1
<220> FEATURE:
<223> OTHER INFORMATION: Domain 1

<400> SEQUENCE: 18

Gly Leu Ile Val Arg Ile Cys Leu Ala Thr Gly Ala Arg Trp Ser Glu
 1               5                  10                  15

Ala Glu Thr Leu Thr Gln Ser Gln Val Met Pro Tyr
            20                  25

<210> SEQ ID NO 19
<211> LENGTH: 38
<212> TYPE: PRT
<213> ORGANISM: Bacteriophage HP1
<220> FEATURE:
<223> OTHER INFORMATION: Domain 2

<400> SEQUENCE: 19

His Val Leu Arg His Thr Phe Ala Ser His Phe Met Met Asn Gly Gly
 1               5                  10                  15

Asn Ile Leu Val Leu Lys Glu Ile Leu Gly His Ser Thr Ile Glu Met
            20                  25                  30

Thr Met Arg Tyr Ala His
        35

<210> SEQ ID NO 20
<211> LENGTH: 28
<212> TYPE: PRT
<213> ORGANISM: Bacteriophage P22
<220> FEATURE:
<223> OTHER INFORMATION: Domain 1

<400> SEQUENCE: 20
```

-continued

```
Lys Ser Val Val Glu Phe Ala Leu Ser Thr Gly Leu Arg Arg Ser Asn
 1               5                  10                  15

Ile Ile Asn Leu Glu Trp Gln Gln Ile Asp Met Gln
            20                  25
```

<210> SEQ ID NO 21
<211> LENGTH: 38
<212> TYPE: PRT
<213> ORGANISM: Bacteriophage P22
<220> FEATURE:
<223> OTHER INFORMATION: Domain 2

<400> SEQUENCE: 21

```
His Asp Leu Arg His Thr Trp Ala Ser Trp Leu Val Gln Ala Gly Val
 1               5                  10                  15

Pro Ile Ser Val Leu Gln Glu Met Gly Gly Trp Glu Ser Ile Glu Met
            20                  25                  30

Val Arg Arg Tyr Ala His
            35
```

<210> SEQ ID NO 22
<211> LENGTH: 28
<212> TYPE: PRT
<213> ORGANISM: Bacteriophage Tn 1545
<220> FEATURE:
<223> OTHER INFORMATION: Domain 1

<400> SEQUENCE: 22

```
Tyr Asp Glu Ile Leu Ile Leu Leu Lys Thr Gly Leu Arg Ile Ser Glu
 1               5                  10                  15

Phe Gly Gly Leu Thr Leu Pro Asp Leu Asp Phe Glu
            20                  25
```

<210> SEQ ID NO 23
<211> LENGTH: 38
<212> TYPE: PRT
<213> ORGANISM: Bacteriophage Tn 1545
<220> FEATURE:
<223> OTHER INFORMATION: Domain 2

<400> SEQUENCE: 23

```
His Ser Leu Arg His Thr Phe Cys Thr Asn Tyr Ala Asn Ala Gly Met
 1               5                  10                  15

Asn Pro Lys Ala Leu Gln Tyr Ile Met Gly His Ala Asn Ile Ala Met
            20                  25                  30

Thr Leu Asn Tyr Tyr Ala
            35
```

<210> SEQ ID NO 24
<211> LENGTH: 28
<212> TYPE: PRT
<213> ORGANISM: Bacteriophage Tn21
<220> FEATURE:
<223> OTHER INFORMATION: Domain 1

<400> SEQUENCE: 24

```
Arg Leu Phe Ala Gln Leu Leu Tyr Gly Thr Gly Met Arg Ile Ser Glu
 1               5                  10                  15

Gly Leu Gln Leu Arg Val Lys Asp Leu Asp Phe Asp
            20                  25
```

<210> SEQ ID NO 25

```
<211> LENGTH: 38
<212> TYPE: PRT
<213> ORGANISM: Bacteriophage Tn21
<220> FEATURE:
<223> OTHER INFORMATION: Domain 2

<400> SEQUENCE: 25
```

His Thr Leu Arg His Ser Phe Ala Thr Ala Leu Leu Arg Ser Gly Tyr
 1               5                  10                  15

Asp Ile Arg Thr Val Gln Asp Leu Leu Gly His Ser Asp Val Ser Thr
            20                  25                  30

Thr Met Ile Tyr Thr His
            35

```
<210> SEQ ID NO 26
<211> LENGTH: 28
<212> TYPE: PRT
<213> ORGANISM: Bacteriophage 154a
<220> FEATURE:
<223> OTHER INFORMATION: Domain 1

<400> SEQUENCE: 26
```

Ala Gly Ala Val Glu Val Gln Ala Leu Thr Gly Met Arg Ile Gly Glu
 1               5                  10                  15

Leu Leu Ala Leu Gln Val Lys Asp Val Asp Leu Lys
            20                  25

```
<210> SEQ ID NO 27
<211> LENGTH: 39
<212> TYPE: PRT
<213> ORGANISM: Bacteriophage 154a
<220> FEATURE:
<223> OTHER INFORMATION: Domain 2

<400> SEQUENCE: 27
```

His Thr Leu Arg His Thr His Ile Ser Leu Leu Ala Glu Met Asn Ile
 1               5                  10                  15

Ser Leu Lys Ala Ile Met Lys Arg Val Gly His Arg Asp Glu Lys Thr
            20                  25                  30

Thr Ile Lys Val Tyr Thr His
            35

```
<210> SEQ ID NO 28
<211> LENGTH: 28
<212> TYPE: PRT
<213> ORGANISM: Bacteriophage lambda
<220> FEATURE:
<223> OTHER INFORMATION: Domain 1

<400> SEQUENCE: 28
```

Arg Leu Ala Met Glu Leu Ala Val Val Thr Gly Gln Arg Val Gly Asp
 1               5                  10                  15

Leu Cys Glu Met Lys Trp Ser Asp Ile Val Asp Gly
            20                  25

```
<210> SEQ ID NO 29
<211> LENGTH: 36
<212> TYPE: PRT
<213> ORGANISM: Bacteriophage lambda
<220> FEATURE:
<223> OTHER INFORMATION: Domain 2

<400> SEQUENCE: 29
```

His Glu Leu Arg Ser Leu Ser Ala Arg Leu Tyr Glu Lys Gln Ile Ser

```
                 1               5                  10                 15
Asp Lys Phe Ala Gln His Leu Leu Gly His Lys Ser Asp Thr Met Ala
                         20                 25                 30

Ser Gln Tyr Arg
            35
```

<210> SEQ ID NO 30
<211> LENGTH: 28
<212> TYPE: PRT
<213> ORGANISM: Bacteriophage 434
<220> FEATURE:
<223> OTHER INFORMATION: Domain 1

<400> SEQUENCE: 30

```
Arg Leu Ala Met Glu Leu Ala Val Val Thr Gly Gln Arg Val Gly Asp
 1               5                  10                 15

Leu Cys Glu Met Lys Trp Ser Asp Ile Val Asp Gly
                20                 25
```

<210> SEQ ID NO 31
<211> LENGTH: 37
<212> TYPE: PRT
<213> ORGANISM: Bacteriophage 434
<220> FEATURE:
<223> OTHER INFORMATION: Domain 2

<400> SEQUENCE: 31

```
His Glu Leu Arg Ser Leu Ser Ala Arg Leu Tyr Glu Lys Gln Ile Ser
 1               5                  10                 15

Asp Lys Phe Ala Gln His Leu Leu Gly His Lys Ser Asp Thr Met Ala
                20                 25                 30

Ser Gln Tyr Arg Asp
            35
```

<210> SEQ ID NO 32
<211> LENGTH: 28
<212> TYPE: PRT
<213> ORGANISM: Bacteriophage L5
<220> FEATURE:
<223> OTHER INFORMATION: Domain 1

<400> SEQUENCE: 32

```
Arg Ile Ala Ala Tyr Ile Leu Ala Trp Thr Ser Leu Arg Phe Gly Glu
 1               5                  10                 15

Leu Ile Glu Leu Arg Arg Lys Asp Ile Val Asp Asp
                20                 25
```

<210> SEQ ID NO 33
<211> LENGTH: 38
<212> TYPE: PRT
<213> ORGANISM: Bacteriophage L5
<220> FEATURE:
<223> OTHER INFORMATION: Domain 2

<400> SEQUENCE: 33

```
His Asp Leu Arg Ala Val Gly Ala Thr Phe Ala Ala Gln Ala Gly Ala
 1               5                  10                 15

Thr Thr Lys Glu Leu Met Ala Arg Leu Gly His Thr Thr Pro Arg Met
                20                 25                 30

Ala Met Lys Tyr Gln Met
            35
```

-continued

```
<210> SEQ ID NO 34
<211> LENGTH: 28
<212> TYPE: PRT
<213> ORGANISM: Bacteriophage FRAT1
<220> FEATURE:
<223> OTHER INFORMATION: Domain 1

<400> SEQUENCE: 34

Arg Val Ala Val Tyr Ile Leu Ala Trp Thr Ser Leu Arg Phe Gly Glu
 1               5                  10                  15

Leu Ile Glu Ile Arg Arg Lys Asp Ile Met Asp Asp
            20                  25

<210> SEQ ID NO 35
<211> LENGTH: 38
<212> TYPE: PRT
<213> ORGANISM: Bacteriophage FRAT1
<220> FEATURE:
<223> OTHER INFORMATION: Domain 2

<400> SEQUENCE: 35

His Asp Leu Arg Ala Val Gly Ala Thr Leu Ala Ala Gln Ala Gly Ala
 1               5                  10                  15

Thr Thr Lys Glu Leu Met Val Arg Leu Gly His Thr Thr Pro Arg Met
            20                  25                  30

Ala Met Lys Tyr Gln Met
        35

<210> SEQ ID NO 36
<211> LENGTH: 28
<212> TYPE: PRT
<213> ORGANISM: Bacteriophage phi-80
<220> FEATURE:
<223> OTHER INFORMATION: Domain 1

<400> SEQUENCE: 36

Val Phe Leu Val Lys Phe Ile Met Leu Thr Gly Cys Arg Thr Ala Glu
 1               5                  10                  15

Ile Arg Leu Ser Glu Arg Ser Trp Phe Arg Leu Asp
            20                  25

<210> SEQ ID NO 37
<211> LENGTH: 38
<212> TYPE: PRT
<213> ORGANISM: Bacteriophage phi-80
<220> FEATURE:
<223> OTHER INFORMATION: Domain 2

<400> SEQUENCE: 37

His Asp Met Arg Arg Thr Ile Ala Thr Asn Leu Ser Glu Leu Gly Cys
 1               5                  10                  15

Pro Pro His Val Ile Glu Lys Leu Leu Gly His Gln Met Val Gly Val
            20                  25                  30

Met Ala His Tyr Asn Leu
        35

<210> SEQ ID NO 38
<211> LENGTH: 28
<212> TYPE: PRT
<213> ORGANISM: Bacteriophage P4
<220> FEATURE:
<223> OTHER INFORMATION: Domain 1

<400> SEQUENCE: 38
```

Arg Ile Ala Val Lys Leu Ser Leu Leu Thr Phe Val Arg Ser Ser Glu
1               5                   10                  15

Leu Arg Phe Ala Arg Trp Asp Glu Phe Asp Phe Asp
                20                  25

<210> SEQ ID NO 39
<211> LENGTH: 40
<212> TYPE: PRT
<213> ORGANISM: Bacteriophage P4
<220> FEATURE:
<223> OTHER INFORMATION: Domain 2

<400> SEQUENCE: 39

His Gly Phe Arg Thr Met Ala Arg Gly Ala Leu Gly Glu Ser Gly Leu
1               5                   10                  15

Trp Ser Asp Asp Ala Ile Glu Arg Gln Leu Ser His Ser Glu Arg Asn
                20                  25                  30

Asn Val Arg Ala Ala Tyr Ile His
            35                  40

<210> SEQ ID NO 40
<211> LENGTH: 28
<212> TYPE: PRT
<213> ORGANISM: Bacteriophage Ms6
<220> FEATURE:
<223> OTHER INFORMATION: Domain 1

<400> SEQUENCE: 40

Lys Leu Met Val Gln Phe Met Val Ser Thr Gly Leu Arg Trp Gly Glu
1               5                   10                  15

Val Ser Ala Leu Gln Pro Arg His Val Asp Leu Glu
                20                  25

<210> SEQ ID NO 41
<211> LENGTH: 39
<212> TYPE: PRT
<213> ORGANISM: Bacteriophage Ms6
<220> FEATURE:
<223> OTHER INFORMATION: Domain 2

<400> SEQUENCE: 41

His Asp Leu Arg His Thr Tyr Ala Ser Trp Gln Leu Thr Gly Gly Thr
1               5                   10                  15

Pro Val Thr Ile Val Ser Arg Gln Leu Gly His Glu Ser Ile Gln Ile
                20                  25                  30

Thr Val Asp Thr Tyr Thr Asp
            35

<210> SEQ ID NO 42
<211> LENGTH: 78
<212> TYPE: DNA
<213> ORGANISM: Bacteriophage Ms6
<220> FEATURE:
<223> OTHER INFORMATION: attP
<221> NAME/KEY: misc_feature
<222> LOCATION: (34)..(59)
<223> OTHER INFORMATION: Core sequence

<400> SEQUENCE: 42
ttcgcaggta aacgcccatt tccccacgat cgaaggggtt cgaatcccct tagctccacc      60
caaaaccgca ggtcagcg                                                   78

<210> SEQ ID NO 43

```
<211> LENGTH: 76
<212> TYPE: DNA
<213> ORGANISM: Mycobacterium smegmatis
<220> FEATURE:
<223> OTHER INFORMATION: attL
<221> NAME/KEY: misc_feature
<222> LOCATION: (32)..(57)
<223> OTHER INFORMATION: Core sequence

<400> SEQUENCE: 43
ggtagcgcac cacactggca gtgtgggggt cagggttcg aatccccta gctccaccca    60 aaaccgcagg tcagcg                                                  76

<210> SEQ ID NO 44
<211> LENGTH: 80
<212> TYPE: DNA
<213> ORGANISM: Mycobacterium smegmatis
<220> FEATURE:
<223> OTHER INFORMATION: attR
<221> NAME/KEY: misc_feature
<222> LOCATION: (34)..(59)
<223> OTHER INFORMATION: Core sequence

<400> SEQUENCE: 44
ttcgcaggta aacgcccatt tccccacgat cgaaggggtt cgaatcccct tagctccact    60
cctcagatac ccgctccggc                                                80

<210> SEQ ID NO 45
<211> LENGTH: 78
<212> TYPE: DNA
<213> ORGANISM: Mycobacterium smegmatis
<220> FEATURE:
<223> OTHER INFORMATION: attB
<221> NAME/KEY: misc_feature
<222> LOCATION: (32)..(57)
<223> OTHER INFORMATION: Core sequence

<400> SEQUENCE: 45
ggtagcgcac cacactggca gtgtgggggt cagggttcg aatccccta gctccactcc    60 tcagataccc gctccggc                                                78

<210> SEQ ID NO 46
<211> LENGTH: 73
<212> TYPE: DNA
<213> ORGANISM: Mycobacterium smegmatis
<220> FEATURE:
<223> OTHER INFORMATION: tRNA ALA
<221> NAME/KEY: modified_base
<222> LOCATION: ()
<223> OTHER INFORMATION: n = p (pseudouridine)

<400> SEQUENCE: 46
ggggctatgg cgcagtdggt agcgcaccac actggcagtg tggggtcag gggtncgaat    60 ccccttagcu cca                                                     73

<210> SEQ ID NO 47
<211> LENGTH: 74
<212> TYPE: DNA
<213> ORGANISM: Mycobacterium smegmatis

<400> SEQUENCE: 47
ggggctatgg cgcagttggt agcgcaccac actggcagtg tggggtcag gggttcgaat    60 ccccttagct ccac                                                    74
```

-continued

<210> SEQ ID NO 48
<211> LENGTH: 74
<212> TYPE: DNA
<213> ORGANISM: Mycobacterium tuberculosis H37rv

<400> SEQUENCE: 48
ggggctatgg cgcagctggt agcgcaccac actggcagtg tgggggtcag gggttcgagt    60
ccccttagct ccac    74

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Integrative
      Expression Plasmid Vector pAV5

<400> SEQUENCE: 49
atggccagga caattgcgga tcccccgggc tgcaggaatt cgatatcaag ctt    53

<210> SEQ ID NO 50
<211> LENGTH: 126
<212> TYPE: DNA
<213> ORGANISM: Artificial Sequence
<220> FEATURE:
<223> OTHER INFORMATION: Description of Artificial Sequence: Integrative
      Expression Plasmid Vector pAV6

<400> SEQUENCE: 50
gtgaagctgg gactgacggt cgcggtagcc ggagccgcca ttctggtcgc aggtctttcc    60
ggatgttcaa gcaacaagtc gactacagga ggatccccg ggctgcagga attcgatatc    120
aagctt    126

<210> SEQ ID NO 51
<211> LENGTH: 162
<212> TYPE: DNA
<213> ORGANISM: Artificial Sequence
<220> FEATURE:
<223> OTHER INFORMATION: Description of Artificial Sequence: Integrative
      Expression Plasmid Vector pAV7

<400> SEQUENCE: 51
atggccacag acgtgagccg aaagattcga gcttggggac gccgattgat gatcggcacg    60
gcagcggctg tagtccttcg gggccgtgtg gggcttgccg gcggagcggc aaccgcgggc    120
ggcgcgggat cccccgggct gcaggaattc gatatcaagc tt    162

<210> SEQ ID NO 52
<211> LENGTH: 252
<212> TYPE: DNA
<213> ORGANISM: Bacteriophage Ms6

<400> SEQUENCE: 52
gatcgccttg tccaacaccc ccgagttcac gttgaacgcc accgaaacca tcacccacgt    60
gtcgttctgg accgacgcca ccggcggggt attcctcgcc tcagcagcag cctcggtcgc    120
caaaggcggc gtgtccgggg acatcatccg catccagacc gcaccatct ccttcaccgg    180 actcgcggcc tgatgtccga ccaccccgac aactacacta tcctcggtat cgaaaaacct    240
ttcccctgga tc    252

<210> SEQ ID NO 53
<211> LENGTH: 450

```
-continued

<212> TYPE: DNA
<213> ORGANISM: Artificial Sequence
<220> FEATURE:
<223> OTHER INFORMATION: Description of Artificial Sequence: Integrative
      expression plasmid vector

<400> SEQUENCE: 53
cctttaatag attatattac taattaattg gggaccctag aggtcccctt tttaaaaatt     60
ttttcacaaa acggtttaca agcataaagc tagtactggg cccgcggatc gccttgtcca    120 acaccccga gttcacgttg aacgccaccg aaaccatcac ccacgtgtcg ttctggaccg     180
acgccaccgg cggggtattc ctcgcctcag cagcagcctc ggtcgccaaa ggcggcgtgt    240
ccggggacat catccgcatc cagaccgcac ccatctcctt caccggactc gcggcctgat    300
gtccgaccac cccgacaact acactatcct cggtatcgaa aaaccttttcc cctggatccg   360 catgcggtac caagcttgat ccgataacac aggaacagat ctatggttcg tgcaaacaaa   420
cgcaacgagg ctctacgaat cggaagcttc                                     450

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 54 caaccgacg gtgttgcg                                                    18
```